US009442104B2

(12) United States Patent
Akahoshi et al.

(10) Patent No.: US 9,442,104 B2
(45) Date of Patent: Sep. 13, 2016

(54) REPORTER VECTOR PRESENTING EXTRACELLULAR BINDING CAPACITY TO METALLIC COMPOUNDS

(75) Inventors: Eiichi Akahoshi, Tokyo (JP); Mitsuko Ishihara, Tokyo (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 667 days.

(21) Appl. No.: 13/429,926

(22) Filed: Mar. 26, 2012

(65) Prior Publication Data
US 2012/0295274 A1    Nov. 22, 2012

(30) Foreign Application Priority Data

Mar. 28, 2011    (JP) .................................. 2011-070799

(51) Int. Cl.
| | | |
|---|---|---|
| A61K 49/16 | (2006.01) | |
| C07K 16/00 | (2006.01) | |
| G01N 33/50 | (2006.01) | |
| A61K 49/18 | (2006.01) | |
| G01N 33/84 | (2006.01) | |
| C12N 15/85 | (2006.01) | |
| C07K 16/44 | (2006.01) | |
| A61K 48/00 | (2006.01) | |

(52) U.S. Cl.
CPC ........... *G01N 33/5005* (2013.01); *A61K 49/16* (2013.01); *A61K 49/1896* (2013.01); *C07K 16/44* (2013.01); *C12N 15/85* (2013.01); *G01N 33/84* (2013.01); *A61K 48/005* (2013.01); *C07K 2317/622* (2013.01); *C07K 2319/02* (2013.01)

(58) Field of Classification Search
None
See application file for complete search history.

(56) References Cited

FOREIGN PATENT DOCUMENTS

WO    WO 2007/135958 A1    11/2007

OTHER PUBLICATIONS

Blake et al., J. Biol. Chem., 271:27677-27685, 1996.*
Assaf A. Gilad, et al., "MRI Report Genes", (Focus on Molecular Imaging), The Journal of Nuclear Medicine, vol. 49, No. 12, Dec. 2008, pp. 1905-1908.
Batya Cohen, et al., "Ferritin as an Endogenous MRI Reporter for Noninvasine Imaging of Gene Expression in C6 Glioma Tumors", Neoplasia, vol. 7, No. 2, Feb. 2005, pp. 109-117.
Mitchell Ho, et al., "Isolation of anti-CD22 Fv with high affinity by Fv display on human cells", PNAS, vol. 103, No. 25, Jun. 20, 2006, pp. 9637-9642.
Abby E. Deans, et al., "Cellular MRI Contrast via Coexpression of Transferrin Receptor and Ferritin", Magnetic Resonance in Medicine, vol. 56, 2006, pp. 51-59.
Office Action issued on Jul. 30, 2013 in the corresponding Japanese Patent Application No. 2011-070799 (with English Translation).
Assaf A. Gilad, et al. "Developing MR reporter genes: promises and pitfalls", NMR Biomed, vol. 20, No. 3, May 2007, pp. 275-290.
pDisplay™ Vector Catalog No. V660-20, Version C, 2002, Invitrogen™ life technologies, pp. 1-10.
Baldari et al, "A novel leader peptide which allows efficient secretion of a fragment of human interleukin 1beta in *Saccharomyces cerevisiae*" , 1987, EMBO Journal, vol. 6, No. 1, pp. 229-234.
Kristiansen et al, "Molecular Dissection of the Intrinsic Factor-Vitamin B Receptor, Cubilin, Discloses Regions Important for Membrane Association and Ligand Binding", 1999, Journal of Biological Chemistry, vol. 274, No. 29, pp. 20540-20544.
pSecTag2 A, B, and C, Catalog No. V900-20 Life technologies™, revision date Jan. 19, 2012.
Mammalian Signal Peptide Vector Set at http://www.sigmaaldrich.com/catalog/product/sigma/pp2379?lang=en® . . . Accessed Dec. 23, 2015 2 pp.
Klatt et al, "Secretory signal peptide modification for optimized antibody-fragment expression-secretion in *Leishmania tarentolae*", 2012, Microbial Cell Factories, vol. 11, No. 97 10 pp.
Chubet et al, "Vectors for Expression and Secretion of FLAG Epitope-Tagged Proteins in Mammalian Cells", 1996, BioTechniques, vol. 20, No. 1, pp. 136-141.

\* cited by examiner

*Primary Examiner* — Nancy T Vogel
(74) *Attorney, Agent, or Firm* — Oblon, McClelland, Maier & Neustadt, L.L.P.

(57) ABSTRACT

According to one embodiment, a reporter vector presenting an extracellular binding capacity to metallic compounds contains a nucleotide sequence exhibiting a promoter activity depending on a specific condition, a nucleotide sequence encoding a metallic compound-binding peptide presented extracellularly, and a nucleotide sequence encoding transcription termination signals.

18 Claims, 6 Drawing Sheets

REPORTER VECTOR PRESENTING EXTRACELLULAR BINDING CAPACITY TO METALLIC COMPOUNDS

CROSS-REFERENCE TO RELATED APPLICATIONS

This application is based upon and claims the benefit of priority from prior Japanese Patent Application No. 2011-070799, filed Mar. 28, 2011, the entire contents of which are incorporated herein by reference.

FIELD

Embodiments described herein relate generally to a reporter vector presenting an extracellular binding capacity to metallic compounds.

BACKGROUND

Owing to aging of the population and an increase in health conscious, medical instruments are essential for our life. Particularly, a magnetic resonance imaging (MRI) technique which gives no damage to a human body and can obtain a tomographic image in the body which cannot be normally visualized, strongly attracts attention in diagnosis in the super-early stage of diseases including cancers.

In MRI diagnosis of diseases, abnormal cells causing diseases are specifically labeled, distinguished from normal cells by the labeling, and imaged. Abnormal cells can be labeled by using, for example, expression of specific genes and proteins, accumulation of metabolites, or the like as an indicator. Particularly, it can be said that since the genes are expressed at a position in an uppermost stream stage of a disease process, the gene expression is the most suitable indicator for diagnosis in the early stage.

One of the methods of labeling abnormal cells using such a gene expression as an indicator is a method of using a reporter gene. In the method, the reporter gene is linked to a downstream of a promoter region of a gene serving as an indicator. When the promoter is activated in an abnormal cell, the reporter gene at the downstream of the promoter is expressed. The cell is directly or indirectly labeled with a product of the expressed reporter gene. As a typical example of the reporter gene, a gene for green fluorescent protein (GFP) to fluorescently label cells is cited. The fluorescently labeled cells are imaged by a device equipped with a fluorescence microscope system.

Some of the reporter genes developed for MRI have been reported. Examples thereof include iron-binding proteins such as ferritin and transferrin. These are an iron-binding reporter gene. The iron-binding reporter gene accumulates iron in a cell in which the iron-binding reporter gene is expressed. The accumulation allows the cell to be labeled with iron. Since an iron imaging effect can be utilized in MRI imaging, a cell labeled with iron accumulated in the cell is detected by the T1- and T2*-weighted image of MRI.

Under such circumstances, in order to achieve an earlier diagnosis, there is a strong demand for development of highly sensitive diagnosis.

DETAILED DESCRIPTION

In general, according to one embodiment, a reporter vector presenting an extracellular binding capacity to metallic compounds is provided.

The reporter vector presenting an extracellular binding capacity to metallic compounds contains a nucleotide sequence exhibiting a promoter activity depending on a specific condition(s), a nucleotide sequence encoding a metallic compound-binding peptide presented extracellularly, and a nucleotide sequence encoding transcription termination signals. The nucleotide sequence encoding a metallic compound-binding peptide presented extracellularly is operably linked to the downstream of the nucleotide sequence exhibiting a promoter activity depending on a specific condition(s). The nucleotide sequence encoding transcription termination signals is operably linked to the downstream of the nucleotide sequence encoding a metallic compound-binding peptide presented extracellularly.

Hereinafter, the reporter vector presenting an extracellular binding capacity to metallic compounds of the embodiment will be described with reference to the drawings.

Figure 1:
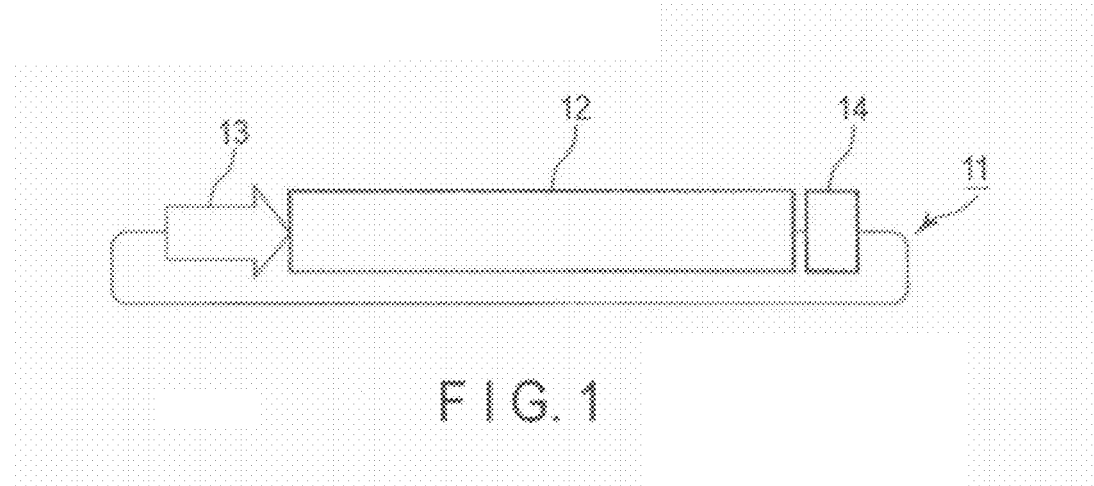
FIG. 1 is a schematic diagram showing a reporter vector presenting an extracellular binding capacity to metallic compounds of one embodiment.

As shown in FIG. 1, a reporter vector presenting an extracellular binding capacity to metallic compounds 11 of the embodiment contains a nucleotide sequence 12 encoding a metallic compound-binding peptide presented extracellularly, a nucleotide sequence 13 exhibiting a promoter activity depending on a specific condition(s), and a nucleotide sequence 14 encoding transcription termination signals.

The reporter vector 11 is a gene construct which is introduced into a target cell or cell population to be used.

The nucleotide sequence 13 exhibits a promoter activity depending on a specific condition(s). The nucleotide sequence 13 is configured to exhibit the promoter activity when the state or environment of the cell into which the reporter vector 11 is introduced satisfies predetermined a specific condition(s). Genes operably linked to the downstream of the nucleotide sequence 13 are expressed by activation of the promoter activity.

The nucleotide sequence 12 encodes a metallic compound-binding peptide presented extracellularly. The nucleotide sequence 12 contains a gene that is configured to be expressed by the promoter activity when the promoter activity of the nucleotide sequence 13 is activated. Therefore, it is configured that when the promoter activity of the nucleotide sequence 13 is activated, a gene encoded by the nucleotide sequence 12 is transcribed and translated in a cell to produce a metallic compound-binding peptide, the produced metallic compound-binding peptide is transferred to a cell membrane, and exhibits extracellular binding capacity to metallic compounds. Therefore, the nucleotide sequence 12 is a reporter gene. Here, the nucleotide sequence 12 may be composed of or contain the reporter gene. That is, the nucleotide sequence 12 functions as a reporter gene whose expression is regulated by the promoter activity of the nucleotide sequence 13 which is activated depending on the state or environment of the introduced cell. Further, a metallic compound-binding peptide, which is encoded by the nucleotide sequence 12, functions as a reporter peptide.

The term "metallic compound-binding peptide" herein is synonymous with "a peptide which binds metallic compounds" and "a peptide which is bound to metallic compounds" and they are exchangeably used.

The nucleotide sequence 14 is configured to terminate transcription of the nucleotide sequence 12 encoding a metallic compound-binding peptide presented extracellularly. For example, the nucleotide sequence 14 is a nucleotide sequence encoding transcription termination signals. The transcription of the nucleotide sequence 12 encoding a metallic compound-binding peptide presented extracellularly is terminated at a suitable position by the presence of the nucleotide sequence 14.

As for the reporter vector 11, the nucleotide sequence 12 encoding a metallic compound-binding peptide presented extracellularly may be operably bound to the downstream of the nucleotide sequence 13 exhibiting a promoter activity depending on a specific condition(s). The nucleotide sequence 14 encoding transcription termination signals may be operably bound to the downstream of the nucleotide sequence 12 encoding a metallic compound-binding peptide presented extracellularly. That is, the reporter vector presenting an extracellular binding capacity to metallic compounds 11 may contain the nucleotide sequence 13 exhibiting a promoter activity depending on a specific condition(s), the nucleotide sequence 12 encoding a metallic compound-binding peptide presented extracellularly, and the nucleotide sequence 14 encoding transcription termination signals in this order from the upstream to the downstream.

The terms "operably bound" and "operably linked" herein are exchangeably used and mean to be bound or linked in a state where an intended function is maintained or a state where the intended function can be exhibited.

The term "presenting an extracellular binding capacity to metallic compounds" herein means that the binding capacity to metallic compounds is given to the outside the cell, for example, the cell surface. Specifically, it is preferable that metallic compound-binding peptides which are encoded by the nucleotide sequence 12 produced in a cell derived from the reporter vector 11 are present intracellularly or extracellularly in a state where the peptides are passed through a cell membrane 22. Metallic compound-binding peptides 23 are peptides which are specifically bound to specific metallic compounds.

Figure 2:
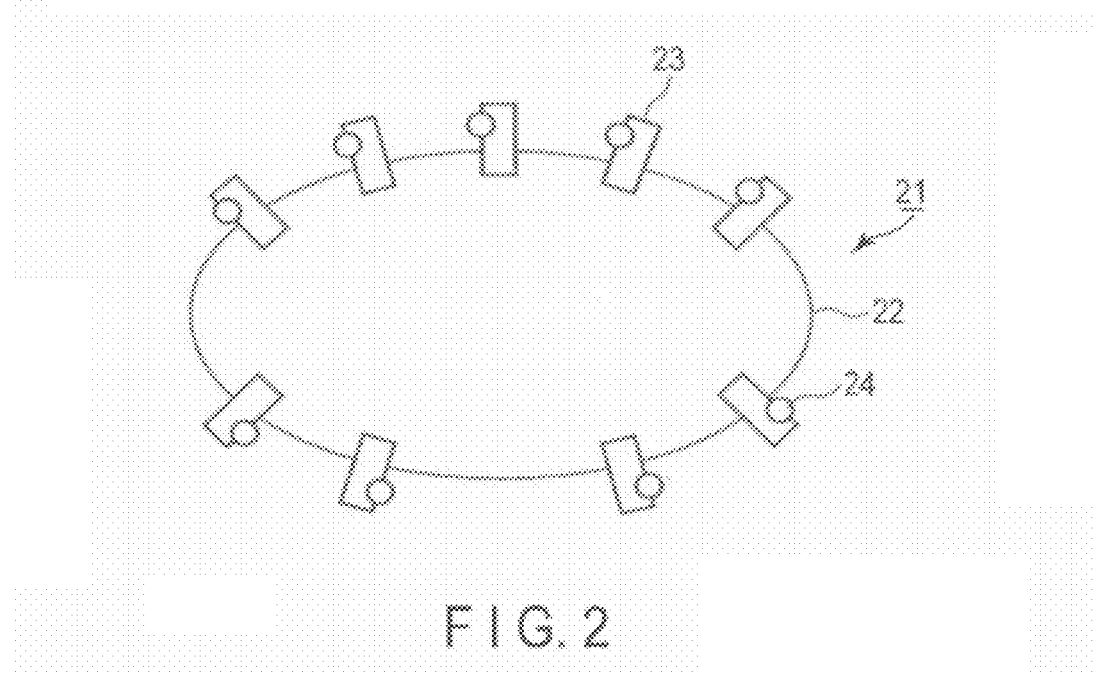
FIG. 2 is a schematic diagram showing a state that reporter presenting an extracellular binding capacity to metallic compounds of one embodiment is extracellularly present.

It should be referred to as FIG. 2. FIG. 2 is a view showing a state where, when the reporter vector 11 is introduced into a cell 21 which satisfies predetermined a specific condition(s), the metallic compound-binding peptides 23 encoded by the nucleotide sequence 12 expressed in the cell 21 are expressed and present intracellularly or extracellularly in a state where the peptides are passed through the cell membrane 22. FIG. 2 is a schematic diagram showing that metallic compounds 24 are specifically bound to the metallic compound-binding peptides 23.

According to the embodiment, a desired metallic compound can be bound to the cell surface by the metallic compound-binding capacity presented extracellularly depending on the conditions of the cell. Thus, the use of devices such as those for magnetic resonance imaging (MRI), positoron emission tomography (PET), single photon emission tomography (SPECT), computerized tomography (CT), and electron spin resonance (ESR) allows the detection of the cell which shows a specific condition(s) to be performed with higher sensitivity. Accordingly, it is possible to perform a desired diagnosis with high sensitivity in an early stage.

Here, the term "a specific condition(s)" of the cell means a specific condition(s) such that the cell itself, for example, "a state" of the inside and/or outside the cell and "an environment" surrounding the cell are determined in advance. Examples of the conditions may include an indicator showing signs of a specific disease, an indicator of the onset of the specific disease, an indicator showing a degree of progression of the onset of the specific disease and/or an indicator showing the severity of the specific disease. For example, the conditions may include conditions regarding an intracellular substance whose content changes associated with the disease onset, the disease presence or the progress degree of the disease. For example, such conditions may be specific indicators, as for the presence of a specific gene, the expression of the specific gene, intracellular and extracellular pH values, information about oxidation reduction, the presence of a specific ion, the presence of an enzyme, the presence of an enzyme substrate, the presence of a specific substance, and the like; the presence or absence of these, the sizes of quantitative values regarding the presences, the presence distribution of the sizes, and/or changes in the presence state, and the like.

Examples of conditions related to genes are as follows. "express only in cells with a specific disease" or "highly express in cells with the specific disease as compared with a normal subject" or "lowly express" may be made a condition. Therefore, for example, under the condition that "genes which express only in cells with a specific disease are present", the promoter activity is exhibited when "genes which express only in cells with a specific disease are present", while the promoter activity is not exhibited when "genes which express only in cells with a specific disease are not present".

For example, when specific conditions are, but not limited to, the canceration of cells and the target cell is a cancer cell, promoters such as fos and myc may be used. When the target cell is a cell associated with abnormal bone metabolism such as arthritis and osteoporosis, promoters such as NFATC1 and CTCC4 may be used. Further, when the target cell is a cell with oxidative stress associated with the initiation of various diseases, promoters such as catalase and SOD may be used. However it does not mean limiting to these examples.

1. Reporter Gene

The reporter vector of one embodiment includes the nucleotide sequence encoding a metallic compound-binding peptide presented extracellularly as the reporter genes. The configuration allows the reporter vector to present the metallic compound-binding peptide as a reporter depending on the promoter activity. As a result, it is possible that metallic compounds can be specifically bound to and/or accumulated in the metallic compound-binding peptide presented extracellularly. Accordingly, the cell is labeled. The cell labeled as described above can be detected by a detection method selected depending on the type of metallic compounds to be bound. That is, the detection is possible by using diagnostic imaging units such as those for magnetic resonance imaging (MRI), positoron emission tomography (PET), single photon emission tomography (SPECT), computerized tomography (CT), and electron spin resonance (ESR) depending on the type of metallic compounds.

The type of metallic compounds to which the reporter peptide is bound may be selected according to a detection means. The term "metallic compounds" herein means substances containing metal atoms from metal particles, metal ions, and metal ion salts, metal complexes, metal complex salts, metal oxides, metal oxide salts, metal hydroxides, metal hydroxide salts, and metal carbonates and hydrates thereof. The "metallic compounds" can be called as "metal atom-containing substances". The metallic compounds have preferably a particle size acceptable as metallic compounds which are used in cells, tissues or animals, particularly individual animals such as mammals, generally as contrast or diagnostic agents. Further, the metallic compounds may be any metallic compound which can be used for diagnostic imaging units such as MRI, PET, SPECT, CT, X-rays, ultrasonic waves, ESR, and DSA and are pharmaceutically acceptable as active substances of the imaging agent. The metallic compounds acceptable as the active substances of the imaging agent are called "contrast metal particles".

For example, when the MRI is used, the metallic compounds may be paramagnetic metals, paramagnetic metal ions, paramagnetic metal complexes, and salts thereof; and paramagnetic metal-containing compounds and derivatives thereof. Specific examples of metallic compounds to be preferably used for MRI include, but not limited to, gadolinium compounds such as gadolinium, gadolinium ions, gadolinium complexes, and salts thereof; terbium compounds such as terbium, terbium ions, terbium complexes, and salts thereof; iron compounds such as iron, iron complexes, and salts thereof; manganese compounds such as manganese, manganese ions, manganese complexes, and salts thereof; manganese compounds containing copper, copper ions, copper complexes, and salts thereof; chromium compounds such as chromium, chromium ions, chromium complexes, and salts thereof; strontium compounds such as strontium, strontium complexes, and salts thereof; copper compounds such as copper, copper complexes, and salts thereof; technetium compounds such as technetium, technetium complexes, and salts thereof; and metal oxides, metal oxide salts, metal hydroxides, or metal carbonates thereof; and derivatives such as hydrates of those compounds. Two or more combinations selected from the group consisting of these compounds may be used. For example, as for the application to MRI, in order to improve the imaging effect by imaging with the device and increase imaging sensitivity of the labeled cell, it is preferable that at least one is selected from the group consisting of gadolinium, gadolinium ions, gadolinium complexes, gadolinium salts, gadolinium complex salts, gadolinium oxides, gadolinium oxide salts, gadolinium hydroxides, gadolinium hydroxide salts, gadolinium carbonates, and hydrates thereof; and the metallic compounds composed of these derivatives.

The selection of the reporter gene may be selected according to the type of metallic compounds to be bound. The peptides encoded by the reporter gene and presented extracellularly may be specifically bound to the metallic compounds selected to be combined for use. The selection of metallic compounds may be selected according to a detection principle or the detection means.

Therefore, the reporter gene includes at least a nucleotide sequence encoding a metallic compound-binding peptide, preferably a nucleotide sequence encoding a metallic compound-binding peptide which can be presented extracellularly.

For example, the metallic compound-binding peptide which can be presented outside the cell may be presented extracellularly through a process of transcribing and translating from genes encoding the peptides, transporting to the cell membrane, and immobilizing to the cell membrane. In addition to the transcription and translation from the gene, the peptide may be arbitrarily modified.

Therefore, more preferably, a nucleotide sequence encoding a signal peptide functioning on the cell membrane transportation of peptides, a nucleotide sequence encoding peptides to be bound to metallic compounds, and a nucleotide sequence encoding an anchor peptide that immobilizes peptides to the cell membrane may be operably linked and included in the reporter gene.

An example of the nucleotide sequence encoding a metallic compound-binding peptide presented extracellularly may contain the following sequences in this order from upstream to downstream;

a nucleotide sequence encoding a metallic compound-binding peptide;

a nucleotide sequence encoding a signal peptide which transports the metallic compound-binding peptide to a cell membrane; and a nucleotide sequence encoding an anchor peptide which immobilizes the metallic compound-binding peptide transported to the cell membrane by the signal peptide on the cell membrane.

a) Nucleotide Sequence Encoding Metallic Compound-Binding Peptide

The metallic compound-binding peptide is preferably a peptide, oligopeptide, polypeptide and/or protein which are specifically bound to a specific metallic compound. As a matter of convenience, peptides, oligopeptides, polypeptides, and proteins are collectively called "peptides". A metallic compound-binding peptide and a metallic compound which is specifically bound to the peptide are recognized as a bound pair.

For example, the sequence encoding peptides which bind metallic compounds may use an antibody gene which is known to be bound to a desired metallic compound or a nucleotide sequence of a single-chain antibody (scFv) gene, and may be designed based on such a nucleotide sequence. The nucleotide sequence may be designed by, for example, modifications and/or alterations such as the substitution, deletion, and addition of some bases in a range that maintains the bindings to metallic compounds, or modification and/or alteration according to subjects being used.

A gene encoding a single-chain antibody peptide can be designed from an amino acid sequence of an antibody which binds metallic compounds.

For example, a gadolinium compound is preferably used because of a high imaging effect in the MRI imaging. Preferable examples of the gadolinium compound include gadolinium, a gadolinium ion, a gadolinium complex, salts and derivatives thereof, derivatives containing any of these, and metallic compounds composed of analogues of gadolinium compounds.

Peptides that are bound to the gadolinium compounds may be antibodies to the gadolinium compounds. For example, a nucleotide sequence encoding a single-chain antibody peptide may be designed from amino acid sequences of the antibodies to the gadolinium compounds.

As an example of a basic antibody in order to design a nucleotide sequence encoding a peptide to be bound to a gadolinium complex, the use of an anti-gadopentetate (hereinafter referred to as "Gd-DTPA") antibody will be described.

Amino acid and nucleotide sequences of a single-chain antibody peptide designed from an amino acid sequence of the Gd-DTPA antibody are described in SEQ ID NO: 1 and SEQ ID NO: 2, respectively.

SEQ ID NO: 1 is an example of an amino acid sequence encoding a peptide to be bound to the gadolinium complex which is produced by linking a light chain variable region ($V_L$) and a heavy chain variable region ($V_H$) of mouse anti-Gd-DTPA monoclonal antibody with a linker peptide.

The amino acid sequence and nucleotide sequence of the light chain variable region ($V_L$) and the heavy chain variable region ($V_H$) of a single-chain antibody which is bound to Gd-DTPA are described in SEQ ID NOS: 3 and 4, and SEQ ID NOS: 5 and 6, respectively. These amino acid sequences and nucleotide sequences do not necessarily need to completely correspond to the sequences described in SEQ ID NOS: 3 to 6 as long as the binding capacity to Gd-DTPA is maintained. Further, amino acid and nucleotide sequences of a single-chain antibody peptide produced by linking these amino acid sequences with the linker peptide do not necessarily need to completely correspond to the sequences described in SEQ ID NO: 1 as long as the binding capacity to Gd-DTPA is maintained. For example, as long as the binding capacity to Gd-DTPA is maintained, modifications such as substitution, deletion, and/or addition may also be included.

The linker peptide is a peptide which is included to achieve binding with gadopentetate utilizing immunological characteristics of the light chain variable region ($V_L$) and heavy chain variable region ($V_H$) of mouse anti-Gd-DTPA monoclonal antibody, and to ligate the light chain variable region ($V_L$) and the heavy chain variable region ($V_H$). Therefore, the length and nucleotide sequence of the linker peptide may not necessarily need to completely correspond to the sequence included in SEQ ID NO: 1. An example of amino acid and nucleotide sequences of the linker peptide are described in SEQ ID NOS: 7 and 8. As long as the amino acid sequence of the linker peptide, for example, exerts binding properties of the single-chain antibody peptide to Gd-DTPA and does not reduce the binding properties, the length and nucleotide sequence may be modified. For example, the nucleotide sequence may be longer or shorter, and further the amino acid sequence may be modified. Alternatively, the linker peptide may be included in order to have a configuration for allowing gadopentetate to be specifically captured by operably binding the light chain variable region ($V_L$) and the heavy chain variable region ($V_H$) of mouse anti-Gd-DTPA monoclonal antibody and utilizing immunological characteristics of the light chain variable region ($V_L$) and the heavy chain variable region ($V_H$).

As described above, the single-chain antibody peptide is produced by linking the light chain variable region ($V_L$) to the heavy chain variable region ($V_H$) with the linker peptide. The order of the light chain variable region ($V_L$) and the heavy chain variable region ($V_H$) via the linker peptide may be arbitrary. That is, it may be "light chain variable region ($V_L$)—linker peptide—heavy chain variable region ($V_H$)" or "heavy chain variable region ($V_H$)—linker peptide—light chain variable region ($V_L$)".

The nucleotide sequence according to SEQ ID NO: 2 is an example of the nucleotide sequence designed from the amino acid sequence according to SEQ ID NO: 1. In the example, the light chain variable region ($V_L$) is linked to the heavy chain variable region ($V_H$) in this order of light chain variable region ($V_L$)—linker peptide—heavy chain variable region ($V_H$). The nucleotide sequence or length of the nucleotide sequence according to SEQ ID NO: 2 may be further modified to the extend possible for achieving the binding with gadopentetate utilizing immunological characteristics of the light chain variable region ($V_L$) and heavy chain variable region ($V_H$) of mouse anti-Gd-DTPA monoclonal antibody. In order to make the sequence to be adapted to a target animal species to be provided, selection of a corresponding codon may be changed.

As an example of a basic antibody in order to design a nucleotide sequence encoding a peptide to be bound to a gadolinium complex, the use of an anti-gadopentetate (hereinafter referred to as "Gd-DTPA") antibody has been described above. According to the description about the example, the nucleotide sequence encoding peptides which bind metallic compounds can be obtained based on antibodies to other desired metallic compounds. That is, in the same way as for gadolinium complex, as for any kind of metallic compounds other than gadolinium compounds or complexes, the nucleotide sequence encoding a metallic compound-binding peptide can be designed and produced from the antibodies. In general, metallic compounds include various kinds of compounds including various kinds of complexes, but as for any of these metallic compounds, similarly, the nucleotide sequence encoding a metallic compound-binding peptide can be designed and produced from the antibodies.

For example, such a single-chain antibody peptide may be produced as follows. First, a monoclonal antibody to a specific metallic compound is produced. Subsequently, a light chain variable region ($V_L$) and a heavy chain variable region ($V_H$) of the antibody are obtained. Further, a linker peptide is designed to have a configuration that specifically captures the specific metallic compound by utilizing immunological characteristics of the light chain variable region ($V_L$) and heavy chain variable region ($V_H$). The light chain variable region ($V_L$), the heavy chain variable region ($V_H$), and the linker peptide are operably bound. Further, the amino acid sequence is specified and a nucleotide sequence encoding the amino acid sequence is obtained. Thus, a nucleotide sequence encoding a single-chain antibody peptide can be obtained. A specific procedure may be performed by a genetic recombination technology known in itself.

The example of the single-chain antibody peptide has been shown above, however, the metallic compound-binding peptide is limited to neither the antibody nor the single-chain antibody peptide. They may be peptides having specific binding properties to specific metallic compounds. Examples thereof may include an oligopeptide composed of three to 20 amino acids, the peptides, oligopeptides, polypeptides, and proteins having other configurations and/or structures, and/or combinations thereof.

b) Signal Peptide

Peptides produced in a cell, namely, peptides obtained by gene transcription and translation and arbitrarily modification are transported to a cell membrane. For example, a signal peptide may be used for transportation to the cell membrane. Examples of the signal peptide include a leader peptide of Ig κ-chain, a leader peptide of preproalbumin, a leader peptide of pre-IgG light chain, a leader peptide of acetylcholine receptor γ subunit precursor, and a nucleotide sequence encoding polyhistidine and polyvaline. However, the signal peptide is not limited thereto.

Here, a nucleotide sequence encoding a signal peptide capable of normally exhibiting a desired function in subjects to be used for the reporter vector, for example, individual animals, organs, tissues, and cells may be used as the signal peptide. Here, the term "capable of normally exhibiting a desired function" indicates "well-functioning as for the movement of peptides and/or proteins to the cell membrane".

Such a nucleotide sequence encoding a signal peptide can be obtained by a known genetic engineering technique such as PCR. Alternatively, the nucleotide sequence may be obtained by chemical synthesis of DNA or a nucleotide sequence which is incorporated into a commercially available vector may be used. As an example of a vector into which a nucleotide sequence encoding the leader peptide of Ig κ-chain is incorporated, pDisplay (Life Technologies) and the like are cited, however it is not limited thereto.

As an example of the signal peptide for transportation of the peptides produced in the cell to the cell membrane, the leader peptide is described herein. However, it is not limited to the leader peptide, any nucleotide sequence may be used as long as it is a nucleotide sequence encoding peptides which can achieve transportation of the peptides produced in the cell to the cell membrane or a nucleotide sequence encoding a signal peptide that is configured to achieve the transportation of peptides transferred and translated in the cell to the cell membrane.

c) Anchor Peptide

As described above, extracellular presence of the metallic compound-binding peptide is achieved by, for example, transporting peptides produced based on the nucleotide sequence encoding a metallic compound-binding peptide in a cell to a cell membrane and immobilizing them to the cell membrane.

Immobilization of peptides to the cell membrane may be achieved by, for example, an anchor peptide. Examples of the anchor peptide include protein domains that immobilize the protein on a cell membrane, for example, transmembrane domains of the membrane proteins, such as a platelet derived growth factor receptor (PDGFR), CD28, CD8, and IgM (generally referred to as "anchor peptide"), and a nucleotide sequence encoding a transmembrane domains of viruses such as lentivirus gp41. However, the anchor peptide is not limited thereto.

Here, a nucleotide sequence encoding an anchor peptide capable of normally exhibiting a desired function in subjects to be used for the reporter vector, for example, individual animals, organs, tissues, and cells may be used as the anchor peptide. Here, the term "capable of normally exhibiting a desired function" indicates "well-functioning as for the immobilization of peptides and/or proteins on the cell membrane".

Such a nucleotide sequence encoding an anchor peptide can be obtained by a known genetic engineering technique such as PCR. Alternatively, the nucleotide sequence may be obtained by chemical synthesis of DNA or a nucleotide sequence which is incorporated into a commercially available vector may be used. As an example of a vector into which a nucleotide sequence encoding the anchor peptide of PDGFR is incorporated, pDisplay (Life Technologies) and the like are cited, however it is not limited thereto.

As an example of a means of immobilizing peptides on the cell membrane in the cell, the anchor peptide has been described herein. However, it is not limited to the anchor peptide. Any nucleotide sequence may be used as long as it may be a nucleotide sequence encoding peptides which can achieve the immobilization of desired peptides or proteins on the cell membrane in the cell or a nucleotide sequence configured to achieve the immobilization of desired peptides or proteins on the cell membrane in the cell.

2. Promoter

The reporter vector of one embodiment includes the nucleotide sequence exhibiting a promoter activity depending on specific conditions. The nucleotide sequence is preferably a nucleotide sequence configured to express a reporter gene which is operably bound to the downstream depending on conditions.

For example, the nucleotide sequence exhibiting a promoter activity depending on specific conditions may be a nucleotide sequence encoding a promoter activated depending on specific conditions, for example, specific conditions of the target cell.

For example, as the promoter of the embodiment, known promoters which are specifically activated in the target cell under specific conditions may be used.

For example, when specific conditions are the canceration of cells and the target cell is a cancer cell, gene promoters such as fos and myc may be used.

Alternatively, when the target cell is a cell associated with abnormal bone metabolism such as arthritis and osteoporosis, for example, promoters such as NFATC1 and CICC4 may be used.

Further, when the target cell is a cell with oxidative stress associated with the initiation of various diseases, promoters such as catalase and SOD may be used.

Cancer cells can be detected by labeling cells which express a reporter gene linked to the nucleotide sequence exhibiting a promoter activity depending on specific conditions with metallic compounds and imaging the target cell with detection devices such as MRI, PET, SPECT, CT, and ESR.

3. Transcription Termination Signal

The reporter vector according to one embodiment includes a nucleotide sequence configured to terminate the transcription started according to conditions as to the reporter gene operably bound to the upstream.

The nucleotide sequence may be a nucleotide sequence which terminates the transcription of the nucleotide sequence on the upstream. For example, it may be the nucleotide sequence encoding transcription termination signals or a nucleotide sequence in itself known as a transcription termination sequence may be used. As an example of the nucleotide sequence, a poly(A) additional signal is cited, however it is not limited thereto.

For example, the poly(A) additional signal may be selected depending on the type of cells into which the reporter vector is introduced and/or animal species from which cells are derived, and configured to function to terminate the transcription of the reporter gene in a cell of interest.

Examples of the sequence which functions in the termination of the transcription of mammal genes include SV40 virus late poly(A) additional signal, bovine growth hormone gene poly(A) additional signal, and the like. However, the poly(A) additional signal which can be used in the embodiment is not limited thereto. The nucleotide sequence may be modified without impairing the function as the poly (A) additional signal.

4. Reporter Peptide

The reporter vector of one embodiment produces a reporter peptide by activating a promoter according to specific conditions and presents extracellular binding capacity to metallic compounds.

As described above, an example of the reporter gene may be produced by operably linking the nucleotide sequence encoding a leader peptide, the nucleotide sequence encoding a metallic compound-binding peptide, and the nucleotide sequence encoding an anchor peptide. The term "operably" herein means that the amino acid sequences encoded by each nucleotide sequence are correctly linked, namely, there is no difference in an amino acid codon frame and a functional peptide, i.e., a metallic compound-binding peptide presented extracellularly is synthesized in the cell into which the nucleotide sequences are introduced. As long as the metallic compound-binding peptide maintains its function, it may be an amino acid sequence except the leader peptide, the metallic compound-binding peptide, and the anchor peptide or may further include amino acid sequences in addition to the leader peptide, the metallic compound-binding peptide, and the anchor peptide. Examples of the amino acid sequences include amino acid sequences such as a hemagglutinin tag sequence and a c-myc tag sequence which make the detection of a fusion protein easy, however they are not limited thereto. Further, the reporter gene and/or the reporter vector may further include nucleotide sequences other than the above sequences.

5. Another Example of Reporter Gene

An example of the nucleotide sequence of the reporter gene according to another embodiment is shown in SEQ ID NO: 10. The reporter gene is a Gd-DTPA-binding single-chain antibody peptide produced by operably linking a nucleotide sequence encoding Ig κ-chain leader peptide, a nucleotide sequence encoding anti-Gd-DTPA single-chain antibody peptide, and a nucleotide sequence encoding anchor peptide of PDGFR.

The reporter gene may be produced by inserting, for example, a gene fragment obtained by digesting the nucleotide sequence of the Gd-DTPA single-chain antibody gene shown in SEQ ID NO: 2 with suitable restriction enzymes such as Bgl II and Sal I into a suitable position of pDisplay (between Bgl II and Sal I). The amino acid sequence of the reporter gene (Gd-DTPA single-chain antibody peptide) described in SEQ ID NO: 10 is shown in SEQ ID NO: 9.

According to another embodiment, an example of the amino acid sequence of the reporter gene is shown in SEQ ID NO: 9. The nucleotide sequence encoding a metallic compound-binding peptide presented extracellularly may be a nucleotide sequence encoding an amino acid sequence represented by SEQ ID NO: 9.

The reporter gene thus produced can be incorporated into the above reporter vector and used. In that case, the reporter vector may include the reporter gene of SEQ ID NO: 10, a suitable promoter operably linked to the upstream, and a nucleotide sequence encoding suitable transcription termination signals which is operably linked to the downstream. This allows a cell in which the promoter has been activated, to be specifically labeled.

6. Reporter Gene Construct

It is preferable that the reporter vector of one embodiment is sent to an intended cell and expresses a reporter gene under detection conditions. Therefore, as long as such a configuration is possible, it may be understood as a reporter gene construct. That is, the reporter gene construct is preferably configured to include a reporter gene which is introduced into a cell and whose expression is regulated by promoter activity of the nucleotide sequence activated depending on the state or environment of the introduced cell and express a reporter gene according to conditions in order to extracellularly present the thus produced reporter peptide as a marker and exhibit binding capacity to metallic compounds.

For example, the reporter gene construct is preferably introduced into a cell by any means known in itself. It may be introduced by the physicochemical procedures such as a method using a cation lipid (lipofection), electroporation, ultrasonic waves, magnetism or a particle gun, or may be constructed in itself as a viral vector such as adenovirus or a plasmid vector in the above manner, or may be constructed in itself as a carrier type such as an ion-complex type of carrier such as cationic lipid, basic polymer, synthetic polypeptide, and apatite carbonate.

An example of the nucleotide sequence encoding a metallic compound-binding peptide presented extracellularly may contain the following sequences in this order from upstream to downstream;

a nucleotide sequence encoding a peptide specifically binding to gadopentetate;

a nucleotide sequence encoding Ig κ-chain leader peptide; and a nucleotide sequence encoding an anchor peptide which immobilizes a platelet-derived growth factor receptor on a cell membrane.

7. Usage Example of Reporter Vector Presenting Extracellular Binding Capacity to Metallic Compounds Usage Example 1

Detection Method

The reporter vector of the embodiment can be used to detect in vitro or in vivo a cell under specific conditions.

In the detection method, the reporter vector is introduced into target individual animals, organs, internal organs, tissues, cell populations and/or a single cell. At the same time as the introduction and/or before and after the introduction, the vector is brought into contact with a metallic compound for forming a binding pair with the reporter peptide presented extracellularly depending on the reporter vector. At the same time as the contact with the metallic compound and/or before and after the contact, the metallic compound specifically bound to the reporter peptide is detected. That is, according to the detection method, it is possible to specifically detect the cell under specific conditions using the presence of the metallic compound as an indicator.

The detection of the metallic compound may be performed a single time, multiple times and/or continuously, and/or may be performed over time.

The method of detecting the metallic compound may be performed using any method known in itself depending on the type of metal atoms in the metallic compound. For example, any method of chemically, physically, physicochemically and/or biochemically detecting metal atoms by using chemical characteristics and/or physical characteristics of metal atoms, which is known in itself, may be used.

When the reporter vector is used, it is possible to present the reporter protein outside the cell, resulting in a highly sensitive detection.

For example, the type of metallic compound for forming a specific binding pair with a reporter peptide which can be measured with diagnostic imaging units, such as MRI, PET, SPECT, CT, and ESR is selected so that the reporter vector can be used in combination with such diagnostic imaging units. In this case, it is possible to more specifically detect cells with higher sensitivity.

An example of the detection method of the embodiment is a method of detecting a cell under specific conditions which includes (1) incorporating a reporter vector presenting an extracellular binding capacity to metallic compounds which includes the nucleotide sequence exhibiting a promoter activity depending on specific conditions, the nucleotide sequence encoding a metallic compound-binding peptide presented extracellularly, and the nucleotide sequence encoding transcription termination signals in this order from the upstream to downstream to be incorporated into a target subject containing a cell;

(2) allowing the metallic compound-binding peptide to be presented outside the cell;

(3) bringing a metal capable of forming a binding pair with the metallic compound-binding peptide into contact with the metallic compound-binding peptide; and (4) detecting the metal bound to the metallic compound-binding peptide.

The target subject containing a cell may be any of individual animals, organs, internal organs, tissues, and cell populations, a single cell collected from the individual animals, and cultured organs, tissues, and cells. After the contact and/or at the same time as the contact with the metal in (3), processes for removing excess metal which is not bound, for example, cleaning, rinsing, diluting, and/or perfusion removal may be performed.

Here, it should be understood that "specific conditions" are "conditions to be detected" which are previously selected to specify "the cell under specific situations". The nucleotide sequence exhibiting a promoter activity depending on specific conditions selects a nucleotide sequence exhibiting a promoter activity under specific conditions in the cell to be detected.

According to the embodiment, a desired metal can be bound on the cell surface by the metallic compound-binding capacity presented extracellularly depending on the conditions of the cell. The cell under specific conditions can be detected with higher sensitivity than that of conventional analyses by utilizing metallic compound-binding capacity presented extracellularly and binding and/or accumulating the metallic compounds.

Usage Example 2

Detection Agent

Any reporter vector above may be provided as the detection agent or the composition for detection, to be used in the detection above.

The detection agent for detecting a specific cell according to the embodiment may include the reporter vector presenting an extracellular binding capacity to metallic compounds which includes the nucleotide sequence exhibiting a promoter activity depending on specific conditions, the nucleotide sequence encoding a metallic compound-binding peptide presented extracellularly, and the nucleotide sequence encoding transcription termination signals in this order from the upstream to downstream as an active substance.

The composition for detecting the specific cell of the embodiment may include the reporter vector presenting an extracellular binding capacity to metallic compounds which includes the nucleotide sequence exhibiting a promoter activity depending on specific conditions, the nucleotide sequence encoding a metallic compound-binding peptide presented extracellularly, and the nucleotide sequence encoding transcription termination signals in this order from the upstream to downstream.

When the detection agent and the composition for detection are applied to individual animals, they may be administered orally, for example, in tablet, liquid formulation form and/or the like, may be administered enterally and/or intravaginally, for example, in liquid and/or suppository form, may be administered intranasally and/or intraocularly in liquid, spray form and/or the like, or may be administered intramuscularly, intravenously, intrathecally, and/or intrathecally in solution and/or suspension form by injection and/or intravenous drip.

When the detection agent or the composition for detection is used, it is possible to present the reporter protein outside the cell, resulting in a highly sensitive detection.

For example, the type of metallic compound for forming a specific binding pair with a reporter peptide, which can be measured with diagnostic imaging units, such as MRI, PET, SPECT, CT, and ESR is selected, for example, so that the reporter vector can be used in combination with such diagnostic imaging units. In this case, it is possible to more specifically detect cells with higher sensitivity. The detection agent and the composition for detection may be understood as an imaging agent and a composition for imaging, respectively. Further, the detection agent and the composition for detection may be provided as kits for detection together with the metallic compound which is derived from the detection agent or the composition for detection and specifically bound to the metallic compound-binding peptide presented extracellularly. For example, the kit for detection includes preferably the reporter vector according to the embodiment and the metallic compound corresponding to the vector. These may be understood as kits for imaging. The metallic compound specifically bound to the metallic compound-binding peptide may included as the metallic compound itself or it may be provided as a pharmaceutically acceptable composition containing the compound as an active substance.

Usage Example 3

Diagnostic Method 1

The reporter vector according to the embodiment can be used to detect in vitro or in vivo a cell under specific conditions.

In the diagnostic method according to another embodiment, the reporter vector is introduced into individual animals, organs, internal organs, tissues, cell populations, a single cell and/or the like, which are to be tested. At the same time as the introduction and/or before and after the introduction, the vector is brought into contact with a metal for forming a binding pair with the reporter peptide of the reporter vector. Before and after the contact and/or at the same time as the contact with the metal, the metal bound to the reporter peptide is detected. Diagnosis of the test subject is performed based on the results of the detected metal. That is, according to the detection method, it is possible to diagnose a disease providing an indication of specific conditions in early stage and/or with high accuracy by specifically detecting the cell under specific conditions using the presence of the metal as an indicator.

The detection of the metal may be performed a single time, multiple times and/or continuously, and/or may be performed over time.

In the diagnosis of the test subject based on the results of the detected metal, it is possible to diagnose the presence or absence of detection of the metal, whether the value of the detected metal is larger or smaller than a preset threshold value, whether the target subject has the disease providing an indication of specific conditions based on information such as changes in the detected value, and the severity of the disease.

The diagnostic method may be used in vivo to be directly performed on an individual animals or may be used in vitro of organs, internal organs, tissues, cell populations and/or a single cell collected from the individual animal.

An example of the method of diagnosing a test subject having a cell under specific conditions according to the embodiment includes:
(1) incorporating the reporter vector presenting an extracellular binding capacity to metallic compounds which includes the nucleotide sequence exhibiting a promoter activity depending on specific conditions, the nucleotide sequence encoding a metallic compound-binding peptide presented extracellularly, and the nucleotide sequence encoding transcription termination signals in this order from the upstream to downstream to be incorporated into a cell in a test subject;
(2) allowing the metallic compound-binding peptide to be presented outside the cell;
(3) bringing a metallic compound capable of forming a binding pair with the metallic compound-binding peptide into contact with the cell;
(4) detecting the metallic compound bound to the metallic compound-binding peptide; and
(5) diagnosing that the test subject has the cell under specific conditions based on the detection results of the metallic compound in (4).

The test subject containing a cell may be any of individual animals; samples collected from organs, internal organs, tissues, cell populations, and a single cell; and cultured tissues and cells. After the contact and/or at the same time as the contact with the metallic compound in (3), processes for removing excess metallic compound which is not bound, for example, cleaning, rinsing, diluting, perfusion removal and/or the like may be performed on the test subject. For example, when the test subject is an individual animal, the excess metallic compound administered to the subject is removed by the blood flow. Accordingly, it is not necessary to remove the excess metallic compound.

As the promoter according to the embodiment, any of the promoters in the embodiments may be used and it may be selected according to the detection conditions.

When the diagnostic method is used, it is possible to present the reporter protein outside the cell, resulting in a highly sensitive diagnosis.

For example, the type of metallic compound for forming a specific binding pair with a reporter peptide, which can be measured with diagnostic imaging units such as MRI, PET, SPECT, CT, and ESR is selected so that the diagnostic method can be used in combination with such diagnostic imaging units. In this case, it is possible to perform diagnosis with higher sensitivity and more specific cell unit.

Usage Example 4

Diagnostic Method 2

According to another embodiment, there is provided a method of diagnosing a disease in a test subject. The usage example is useful, particularly to diagnose a disease of an individual animal.

The method of diagnosing a disease in a test subject includes:
(1) incorporating the reporter vector presenting an extracellular binding capacity to metallic compounds which includes the nucleotide sequence exhibiting a promoter activity depending on specific conditions, the nucleotide sequence encoding a metallic compound-binding peptide presented extracellularly, and the nucleotide sequence encoding transcription termination signals in this order from the upstream to downstream to be incorporated into a cell in a test subject;
(2) allowing the metallic compound-binding peptide to be presented outside the cell;
(3) bringing a metallic compound capable of forming a binding pair with the metallic compound-binding peptide into contact with the cell;
(4) detecting the metallic compound bound to the metallic compound-binding peptide; and
(5) diagnosing the disease in the test subject based on the detection results of the metallic compound in (4).

Basically, matters other than the above procedures may be the same as those described in the detection method of Usage example 1 and the diagnostic method 1 of Usage example 3. As a means of making the reporter vector incorporated into a cell in a test subject, for example, the dosage forms and the routes of administration to individual animals described in the detection agent of Usage example 2 above may be used. Preferably, the reporter vector is administered intravenously to an individual animal which is the test subject, to allow the reporter vector to be incorporated into cells of the individual animal.

Here, "specific conditions" are "conditions to be detected" which are previously selected to specify "the cell under specific situations", and "specific conditions" are conditions providing "an indication of the disease to be detected", namely "an indication of a specific disease". That is, as the promoter according to the embodiment, a promoter which is specifically activated under the condition of being specifically present in the disease being detected in the test subject may be used. For example, in order to diagnose cancers, promoters such as fos and myc may be used. In order to diagnose diseases associated with abnormal bone metabolism such as arthritis and osteoporosis, promoters such as NFATC1 and CICC4 may be used. Promoters such as catalase and SOD may be used to diagnose diseases associated with oxidative stress. Alternatively, a gene which is specifically expressed by the onset of a specific disease may be used or any of such genes known in themselves may be used.

Here, the "test subject" may be any of individual animals such as mammals (mainly including humans), livestock, pet animals, and industrial animals, or may be organs, internal organs, tissues, cell populations and/or a single cell obtained from the test subject.

According to the embodiment, a desired metallic compound can be bound on the cell surface by the metallic compound-binding capacity presented extracellularly depending on the conditions of the cell derived from the specific disease. It is possible to perform diagnosis with higher sensitivity than that of conventional diagnoses by utilizing the metallic compound-binding capacity presented extracellularly and binding and/or accumulating the metallic compounds. Thus, it is possible to diagnose the presence, onset, and sign of disease in very early stage.

For example, the type of metallic compound for forming a specific binding pair with a reporter peptide, which can be measured with diagnostic imaging units such as MRI, PET, SPECT, CT, and ESR is selected so that the diagnostic method can be used in combination with such diagnostic imaging units. In this case, it is possible to perform diagnosis with higher sensitivity and more specific cell unit.

Usage Example 5

Diagnostic Agent

Any reporter vector above may be provided as the diagnostic agent or diagnostic composition to be used in the diagnosis.

The diagnostic agent according to the embodiment may be a diagnostic agent for the disease providing an indication of specific conditions which includes the reporter vector presenting an extracellular binding capacity to metallic compounds which includes the nucleotide sequence exhibiting a promoter activity depending on specific conditions, the nucleotide sequence encoding a metallic compound-binding peptide presented extracellularly, and the nucleotide sequence encoding transcription termination signals in this order from the upstream to downstream as an active substance.

The diagnostic composition according to the embodiment may be a diagnostic composition for the disease providing an indication of specific conditions, which includes the reporter vector presenting an extracellular binding capacity to metallic compounds which includes the nucleotide sequence exhibiting a promoter activity depending on specific conditions, the nucleotide sequence encoding a metallic compound-binding peptide presented extracellularly, and the nucleotide sequence encoding transcription termination signals in this order from the upstream to downstream as an active substance.

The diagnostic agent and the diagnostic composition may be administered to a subject to be diagnosed in the dosage forms and the routes of administration described in the detection agent of Usage example 2 above. Further, the diagnostic agent and the diagnostic composition may be provided as kits for diagnosis together with the metallic compound which is derived from the diagnostic agent or the diagnostic composition and specifically bound to the metallic compound-binding peptide presented extracellularly. For example, the diagnostic kit includes preferably the reporter vector according to the embodiment and the metallic compound corresponding to the vector. These may be understood as kits for imaging. The metallic compound specifically bound to the metallic compound-binding peptide may included as the metallic compound itself or it may be provided as a pharmaceutically acceptable composition containing the compound as an active substance.

According to the embodiment, a desired metallic compound can be bound to the cell surface by the binding capacity to metallic compounds presented extracellularly depending on the conditions of the cell derived from the specific disease. It is possible to perform diagnosis with higher sensitivity than that of conventional diagnoses by utilizing the binding capacity to metallic compounds presented extracellularly, and binding and/or accumulating the metallic compounds. Thus, it is possible to diagnose the presence, onset, and sign of disease in very early stage.

For example, the type of metallic compound for forming a specific binding pair with a reporter peptide, which can be measured with diagnostic imaging units, such as MRI, PET, SPECT, CT, and ESR is selected so that the diagnostic agent or the diagnostic composition can be used in combination with such diagnostic imaging units. In this case, it is possible to perform diagnosis with higher sensitivity and more specific cell unit.

Usage Example 6

Treatment Method

The reporter vector according to the embodiment can be used for the diagnostic methods described in Diagnostic methods 1 and 2 and further can be used as a treatment method.

In a method of treating a specific disease according to the embodiment, the reporter vector is introduced into a subject to be treated. At the same time as the introduction and/or before and after the introduction, the vector is brought into contact with a metallic compound for forming a binding pair with the reporter peptide of the reporter vector. After the contact with the metallic compound, energy is added to the metallic compound bound to the reporter peptide in order to destroy the cell in which the reporter peptide is presented extracellularly. Since high energy can be focused as compared with the case of living organisms, it is possible to selectively destroy only the cell in which the reporter peptide bound to the metallic compound is presented extracellularly.

Examples of the energy may include electrical energy such as high frequency, low frequency, and electromagnetic waves; and nuclear physics energy such as thermal energy and radiation. For example, it is possible to treat by using, but not limited to, a hyperthermia (thermal therapy) device such as Thermotron, Novalis referred to as linac, a cyberknife, a linear accelerator for tomotheraphy, a neutron capture therapy (BNCT) device, and a heavy particle radiotherapy device.

Energy load to metallic compound may be conducted a single time, multiple times or continuously.

For example, the method of treating a specific disease according to the embodiment includes:
(1) incorporating the reporter vector presenting an extracellular binding capacity to metallic compounds which includes the nucleotide sequence exhibiting a promoter activity depending on specific conditions, the nucleotide sequence encoding a metallic compound-binding peptide presented extracellularly, and the nucleotide sequence encoding transcription termination signals in this order from the upstream to downstream to be incorporated into a cell in a test subject;
(2) allowing the metallic compound-binding peptide to be presented outside the cell;
(3) bringing a metallic compound capable of forming a binding pair with the metallic compound-binding peptide into contact with the cell; and
(4) applying energy to the metallic compound bound to the metallic compound-binding peptide to specifically destroy the cell expressing the reporter peptide.

Here, "specific conditions" are "conditions resulting from a specific disease" or conditions providing "an indication of a specific disease". That is, as the promoter according to the embodiment, a promoter which is specifically activated under the condition of being specifically present in the test subject with the disease being detected may be used. For example, in order to diagnose cancers, promoters such as fos and myc may be used. In order to diagnose diseases associated with abnormal bone metabolism such as arthritis and osteoporosis, promoters such as NFATC1 and CICC4 may be used. Promoters such as catalase and SOD may be used to diagnose diseases associated with oxidative stress. Alternatively, a gene which is specifically expressed by the onset of a specific disease may be used or any of such genes known in themselves may be used.

Here, the "test subject" may be any of individual animals such as mammals (mainly including humans), livestock, pet animals, and industrial animals, or may be organs, internal organs, tissues, cell populations and/or a single cell obtained from the test subject.

The treatment method may be performed continuously, for example, after detecting and specifying a focus by the detection method and the diagnostic method to be performed by using the reporter vector. Accordingly, it is possible to specifically treat only the focus which has been detected early at an early stage.

Usage Example 7

Therapeutic Aid

Any reporter vector above may be provided as the therapeutic aid or composition for therapeutic aid to be used in the treatment.

The therapeutic aid according to the embodiment may be a therapeutic aid to treat the disease associated with specific conditions, which includes the reporter vector presenting an extracellular binding capacity to metallic compounds which includes the nucleotide sequence exhibiting a promoter activity depending on specific conditions, the nucleotide sequence encoding a metallic compound-binding peptide presented extracellularly, and the nucleotide sequence encoding transcription termination signals in this order from the upstream to downstream as an active substance.

The diagnostic composition according to the embodiment may be a composition for therapeutic aid to treat the disease associated with specific conditions, which includes the reporter vector presenting an extracellular binding capacity to metallic compounds which includes the nucleotide sequence exhibiting a promoter activity depending on specific conditions, the nucleotide sequence encoding a metallic compound-binding peptide presented extracellularly, and the nucleotide sequence encoding transcription termination signals in this order from the upstream to downstream as an active substance.

The therapeutic aid and the composition for therapeutic aid may be administered to a subject to be diagnosed in the dosage forms and the routes of administration described in the detection agent of Usage example 2 above.

The therapeutic aid and the composition for therapeutic aid may be administered as a single drug or in combination with any known anticancer therapy. Such an anticancer therapy may be, for example, radiotherapy or chemotherapy. Further, the therapeutic aid and the composition for therapeutic aid may be provided as kits for therapy together with the metallic compound which is derived from the therapeutic aid or the composition for therapeutic aid and specifically bound to the metallic compound-binding peptide presented extracellularly. For example, the diagnostic kit includes preferably the reporter vector according to the embodiment and the metallic compound corresponding to the vector. The metallic compound specifically bound to the metallic compound-binding peptide may included as the metallic compound itself or it may be included as a pharmaceutically acceptable composition containing the compound as an active substance.

The therapeutic aid and the composition for therapeutic aid may be used continuously, for example, after detecting and specifying a focus by the detection method and the diagnostic method to be performed using the reporter vector. Accordingly, it is possible to specifically treat only the focus which has been detected early at an early stage. Thus, the test subject is diagnosed based on the detection results of the metallic compound. That is, according to the detection method, it is possible to treat the disease providing an indication of specific conditions in earlier stage and/or with higher accuracy by specifically detecting the cell under specific conditions by using the presence of the metallic compound as an indicator.

For example, the therapeutic aid and the composition for therapeutic aid can be utilized by selecting the type of metallic compound for forming a specific binding pair with a reporter peptide, which can be measured with diagnostic imaging units, such as MRI, PET, SPECT, CT, and ESR is selected and by using in combination with therapeutic devices such as a hyperthermia device, a linear accelerator, a neutron capture therapy device (BNCT device) and a heavy particle radiotherapy device, or selecting the type of metallic compound which can be measured with these devices. In this case, it is possible to perform treatment with higher accuracy and more specific cell unit. The therapeutic aid and the composition for therapeutic aid may be understood as an imaging therapeutic aid and the composition for imaging therapeutic aid, respectively.

EXAMPLES

Hereinafter, one example of the embodiments will be more specifically described with reference to Examples. The following examples are intended to explain one example of the embodiments and are not intended to limit the scope of the present invention.

1) Production of Anti-Gadolinium DTPA Single-Chain Antibody Gene

An amino acid sequence of anti-Gd-DTPA single-chain antibody (Gd-scFv) was designed by linking a light chain variable region ($V_L$) and a heavy chain variable region ($V_H$) of anti-Gd-DTPA monoclonal antibody (anti-Gd-DTPA mAb) with a linker peptide (SEQ ID NO: 1). Based on the amino acid sequence, a nucleotide sequence was optimized for human codon usage and a Gd-scFv gene was chemically synthesized (SEQ ID NO: 2).

2) Production of GdscFv Gene-Incorporated Vector (pDis-GdscFv)

Figure 3:
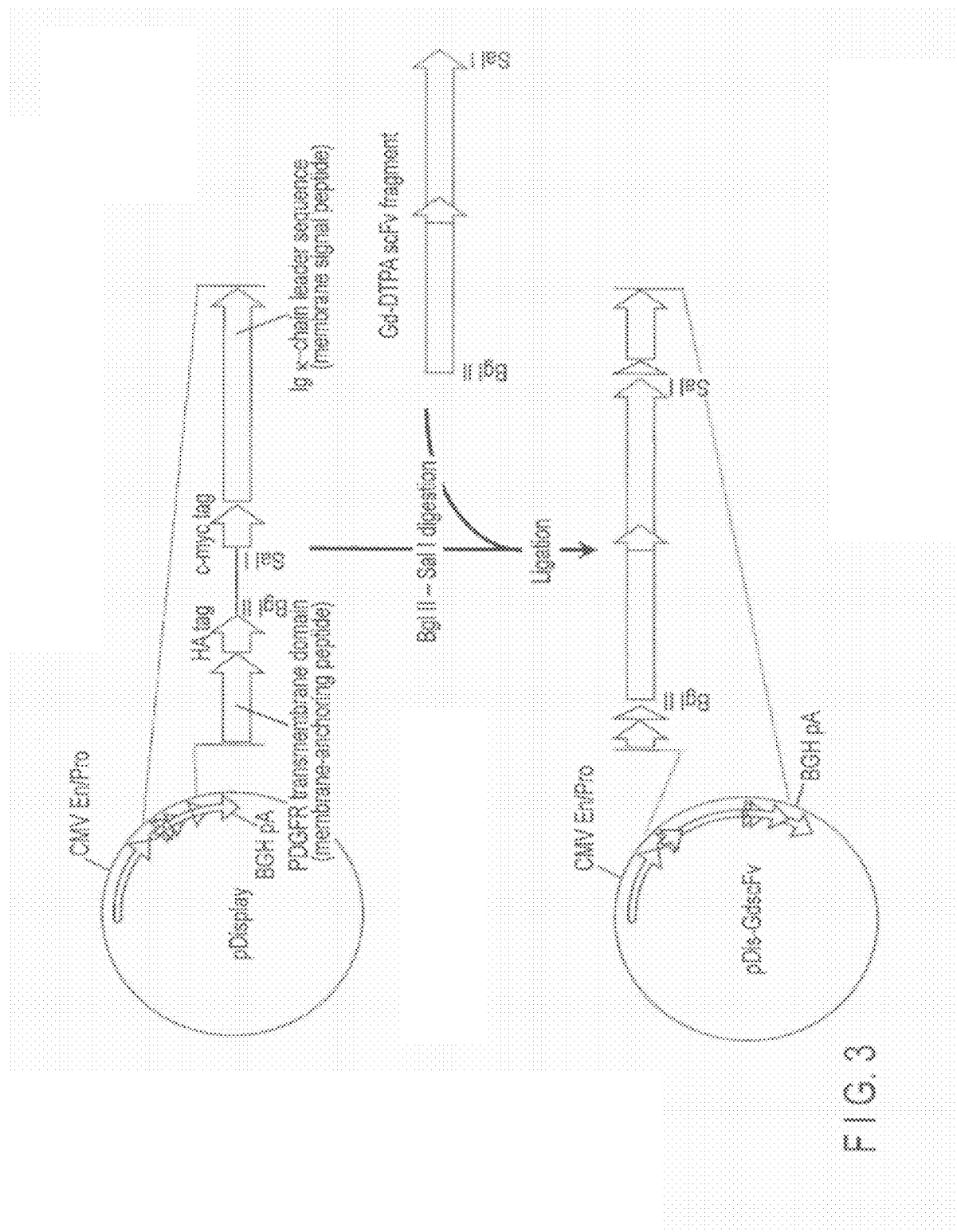
FIG. 3 is a schematic diagram showing the reporter vector presenting an extracellular binding capacity to metallic compounds of one embodiment.

In order to capture Gd-DTPA outside the cell, a vector designed so that Gd-scFv as a fusion protein was presented on the cell surface was produced. pDisplay (Life Technologies) is a vector into which a signal peptide which transports the protein to the cell membrane and an anchor peptide which immobilizes the protein transported to the cell membrane on the membrane are incorporated. Incorporation of an objective gene into both peptides enables a gene product as a fusion protein to be immobilized on the cell membrane and to be presented on the cell surface. Additionally, a hemagglutinin (HA) tag sequence for making the detection of the fusion protein easy and a c-myc tag sequence are incorporated into the pDisplay. The pDisplay was used to produce a GdscFv gene-incorporated vector (pDis-GdscFv). The GdscFv gene synthesized by the method described in 1) was digested with restriction enzymes (Bgl II and Sal I) and the resultant gene was inserted into the pDisplay vector digested with the restriction enzymes (Bgl II and Sal I) to produce a pDis-GdscFv (FIG. 3). A nucleotide sequence of the GdscFv fusion gene of pDis-GdscFv is described in SEQ ID NO: 10 and an amino acid sequence of a fusion protein encoded by the gene is described in SEQ ID NO: 9.

3) Detection of GdscFv Protein by Western Blot

Figure 4:
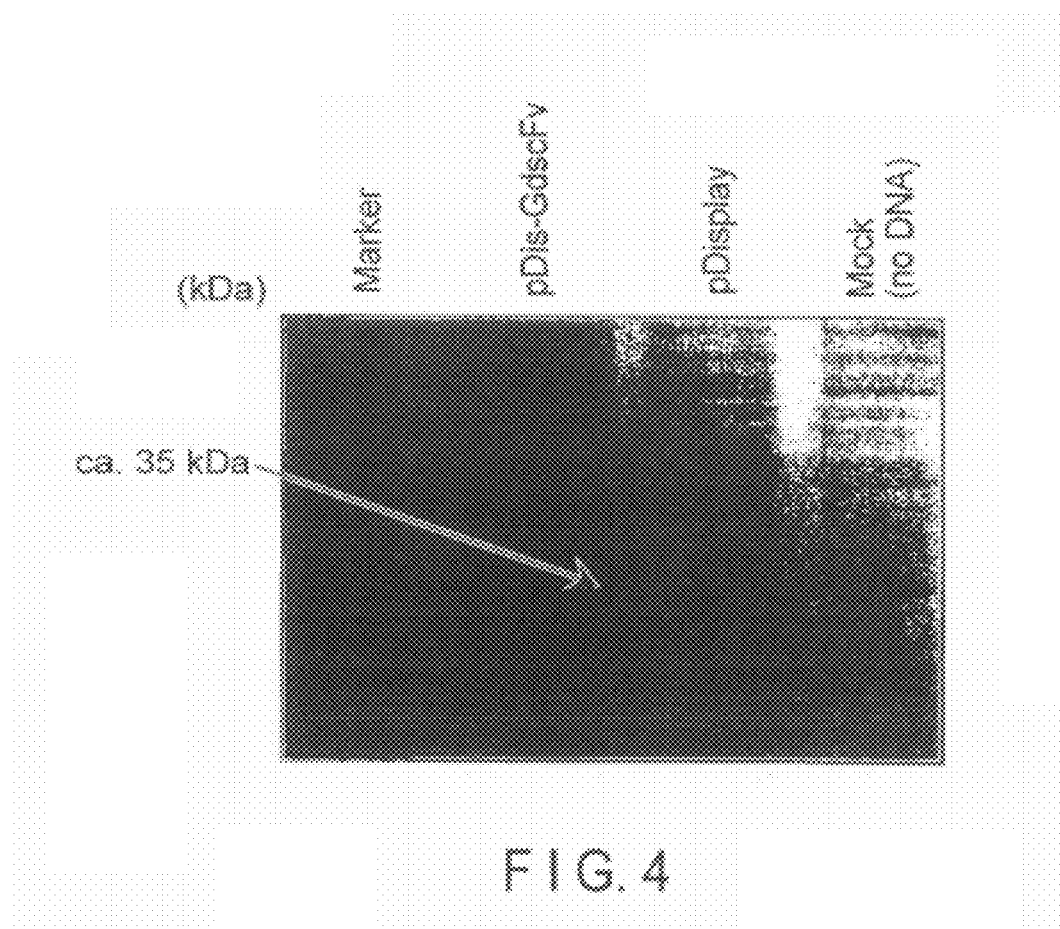
FIG. 4 is a view showing results of detection of a GdscFv protein by Western blot analysis in Example.

50 μL of lipofectamine 2000 was added to 1.0 μL of Opti-MEM medium which was allowed to stand at room temperature for 5 minutes. The resultant product was mixed with 50 μL of Opti-MEM medium containing 0.6 μg of vector (pDis-GdscFv or pDisplay) and the mixture was allowed to stand at room temperature for 20 minutes. Then, the resultant solution was added to a culture medium of Huh-7 cells cultured overnight (seeded in a 24-well plate at a density of $8.0 \times 10^4$ cells per well) and continuously cultured. The medium was removed in 48 hours and the cells were washed with PBS twice. Thereafter, the cells were peeled off from the bottom surface of the plate using a cell scraper and they were suspended in PBS. The cells were recovered by centrifugation at 14,000 rpm for 5 minutes and a cell lysate (1×SDS-PAGE buffer) was added thereto, which was incubated in boiling water for 5 minutes, followed by 8% SDS-polyacrylamide gel electrophoresis. After the end of the electrophoresis, the proteins in the gel were blotted to a PVDF membrane (Pore size: 0.44 µm, Millipore) by using a submarine-type electrophoresis device. After blocking of the PVDF membrane with Block ace (Dainippon Sumitomo Pharma), the membrane was immersed in a primary antibody solution (PBS containing a primary antibody 500-fold diluted and 10% goat normal serum) and gently shaken at room temperature for one hour. As the primary antibody, a mouse anti-HA antibody recognizing the hemagglutinin tag sequence in the GdscFv fusion protein (Millipore) was used. After one hour, the primary antibody solution was removed, the membrane was washed with Tris-buffered saline (TBS) three times. Then, the protein to which the primary antibody was bound was detected using ABC kit (Alkaline Phosphatase Universal, VECTASTAIN). The operation was performed in accordance with the instruction manual of the kit. The PVDF membrane was color-developed with BCIP/NBT(KPL) which was a substrate of alkaline phosphatase. As shown in FIG. 4, a signal derived from the Gd-scFv fusion protein (a band indicated by an arrow, molecular weight: about 35 kDa) was detected in the cell with the pDis-GdscFv introduced.

4) Detection of GdscFv Protein by Immunocyte Staining

Figure 5:
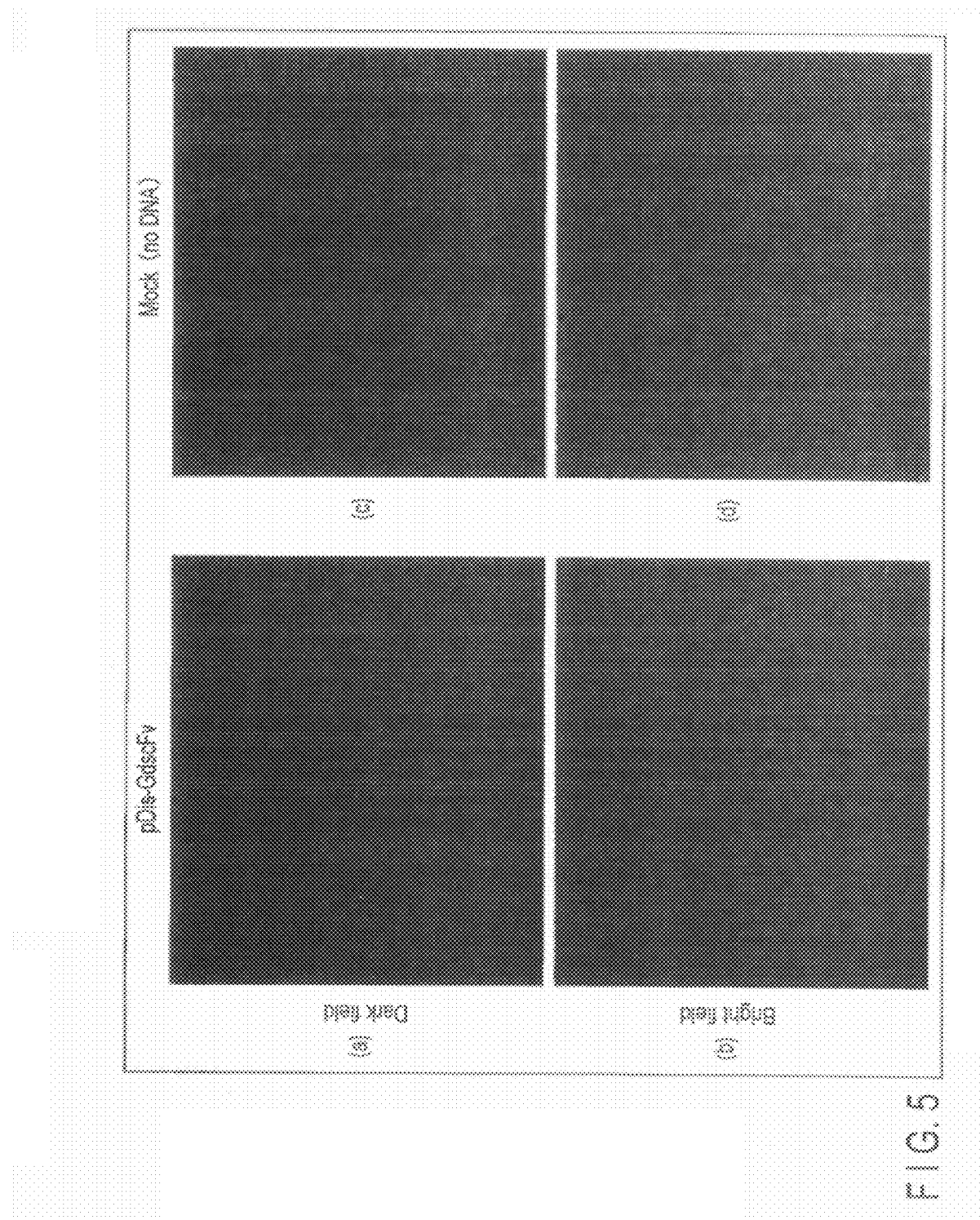
FIG. 5 is a view showing results of detection of the GdscFv protein by immunocyte staining in Example.

50 µL of lipofectamine 2000 was added with 1.0 µL of Opti-MEM medium which was allowed to stand at room temperature for 5 minutes. The resultant product was mixed with 50 µL of Opti-MEM medium containing 0.6 µg of vector (pDis-GdscFv or pDisplay) and the mixture was allowed to stand at room temperature for 20 minutes. Then, the resultant solution was added to a culture medium of Huh-7 cells cultured overnight (seeded in an 8-well chamber slide at a density of $4.0 \times 10^4$ cells per well) and continuously cultured. The medium was removed in 48 hours and the cells were washed with PBS twice. Thereafter, 300 µL of 4% paraformaldehyde was added thereto, and reacted at room temperature for 20 minutes. After washing the cells with PBS three times, 500 µL of a blocking solution (PBS containing 5% goat normal serum) was added and allowed to stand at room temperature. The blocking solution was removed in one hour, a primary antibody solution (PBS containing a primary antibody 250-fold diluted and 5% goat normal serum) was added thereto. As the primary antibody, a mouse anti-c-myc antibody recognizing the c-myc tag sequence in the GdscFv fusion protein (Sigma) was used. After being allowed to stand at 4° C. overnight, the primary antibody solution was removed, the cells were washed with PBS three times, followed by reaction with a secondary antibody solution (a fluorescently labeled (Alexa 555 label) goat anti-mouse monoclonal antibody 1000-fold diluted, Life Technologies) at room temperature. The secondary antibody solution was removed in one hour and the cells were washed with PBS twice. Thereafter, the cells were nuclear-stained with a DAPI solution (1 µg/ml). After washing with PBS twice, the chamber was removed and a drop of a mounting agent AntiFade (Life Technologies) was put thereon. A cover glass was placed on the mounting agent and the four sides thereof were fixed with nail polish, followed by observation with an inverted microscope equipped with a fluorescence device. As shown in FIG. 5, fluorescence derived from the Gd-scFv fusion protein was detected in cells into which the pDis-GdscFv was introduced (FIG. 5).

Figure 6:
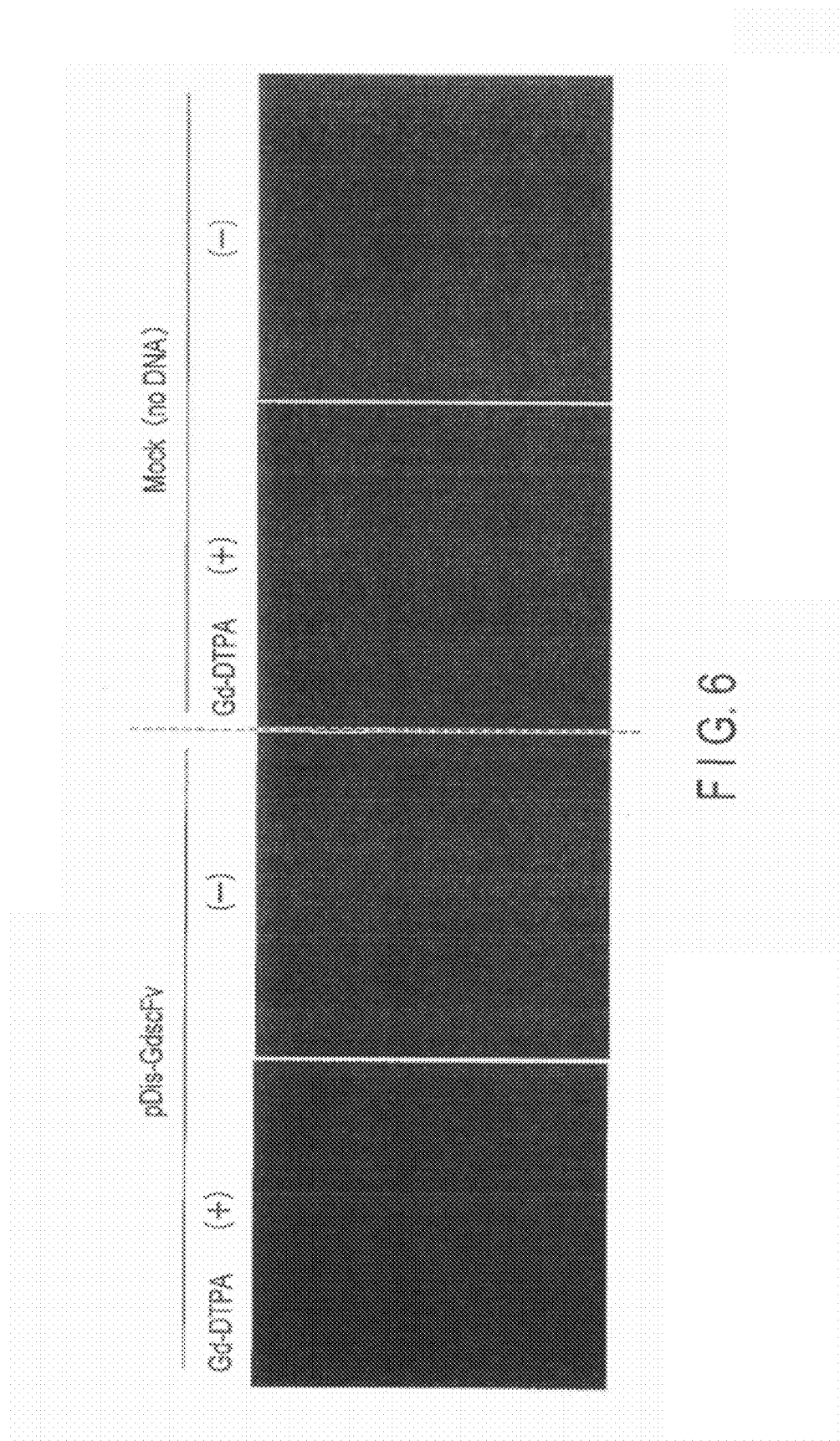
FIG. 6 is a view showing a binding of an MR imaging agent (gadopentetate) to GdscFv-expressing cells in Example.

5) Detection of Binding of MR Contrast Agent (Gadopentetate) to GdscFv-Expressing Cells Huh-7 cells into which the pDis-GdscFv was introduced by the method described in 3) (Gd-scFv cells) and Huh-7 cells which was treated in the same manner as the above cells except that no vector was introduced (Mock cells) were prepared. The medium was removed in 48 hours and the cells were washed with PBS. Thereafter, PBS containing 8% goat normal serum was added thereto, followed by blocking at room temperature for 30 minutes. The solution was removed in 30 minutes. A mixture of gadopentetate (Gd-DTPA and BioPAL) labeled with horseradish peroxidase (HRP) and rabbit anti-HRP antibody (fluorescently-labeled antibody) (SEIKAGAKU BIOBUSSINESS) labeled with fluorescent dye (DyLight 488) or only the fluorescently-labeled antibody was added to the cells, which was reacted at room temperature for one hour. The HRP-Gd-DTPA and the DyLight 488-labeled HRP antibody were previously incubated in PBS containing 5% goat normal serum at room temperature for 30 minutes to form a composite and then the composite was added. After one hour, the cells were washed with PBS twice. A sample for fluorescent observation was produced in the same manner after the nuclear staining as described in 4), followed by observation with an upright epifluorescent microscope. As shown in FIG. 6, fluorescence derived from Gd-DTPA/fluorescently-labeled antibody was detected in cells into which the pDis-GdscFv was introduced (FIG. 6).

6) Effect of Contrast-Enhanced MR Imaging in GdscFv-Expressing Cells (Detection by Micro-MRI)

Figure 7:
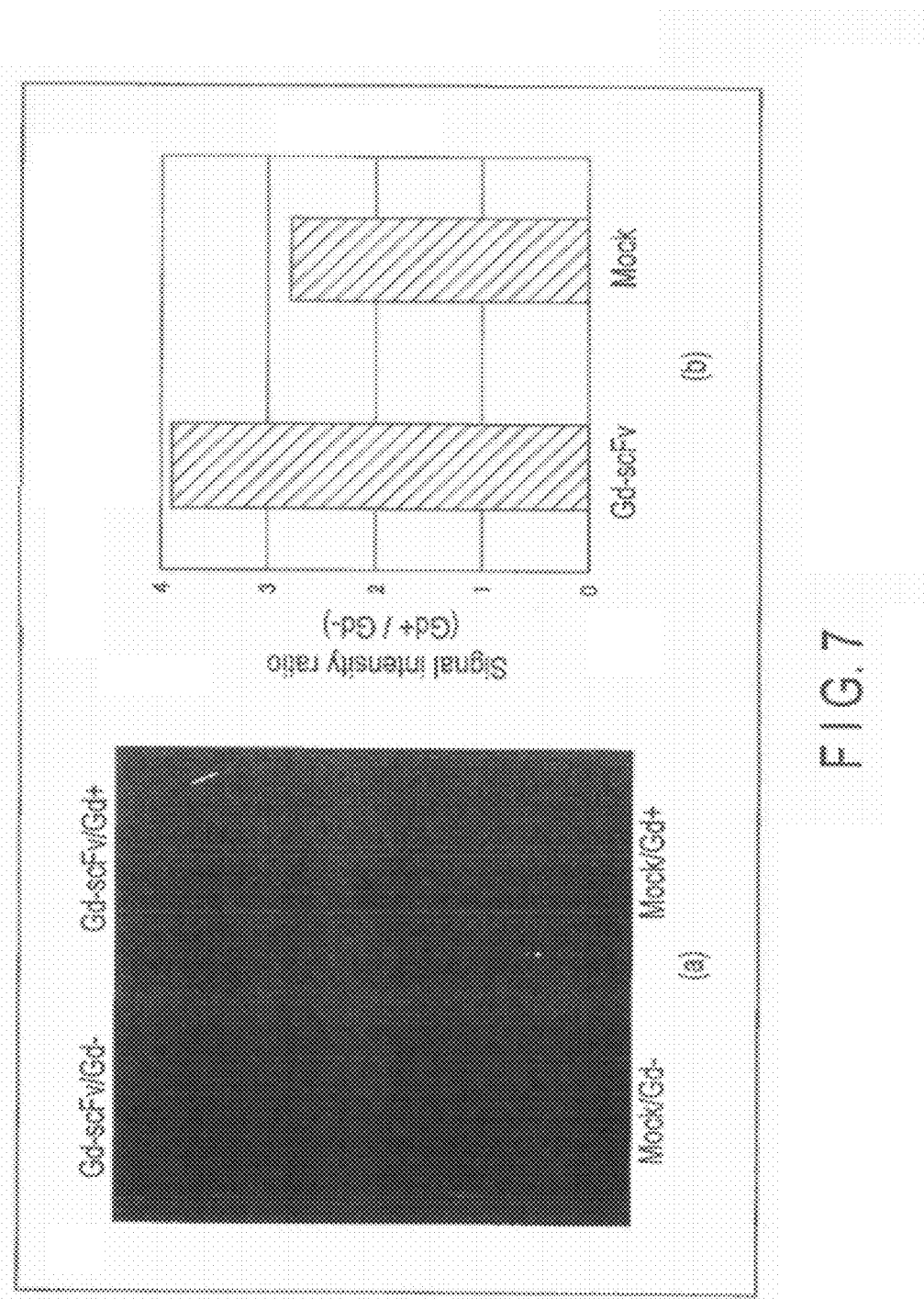
FIG. 7 is a view showing contrast enhancement effects on an MR image of the GdscFv-expressing cells obtained in Example.

Huh-7 cells (Gd-scFv cells) into which the pDis-GdscFv was introduced by the method described in 3) were recovered by 0.25% trypsin treatment. In this case, Huh-7 cells (Mock cells) obtained in the same manner as the above cells except that the vector was not introduced were prepared. The recovered Gd-scFv cells and Mock cells were separated into two populations. Thereafter, a total of four samples (Gd-scFv cell/Gd+, Gd-scFv cell/Gd-, Mock cell/Gd+, and Mock cell/Gd-) were prepared by adding 10 µg/mL of a medium containing Gd-DTPA to one of the populations and adding 500 µL of a medium not containing Gd-DTPA to the other. Then, the samples were incubated at 37° C. while shaking gently. After two hours, the cells were recovered by centrifugation at 1,000 rpm for three minutes, followed by washing of the cells with of 1 mL of PBS. The cells were suspended in 350 µL of PBS warmed to 40° C. in advance and the suspension was added to 350 µL of 2.0% agarose warmed to 40° C., which was mixed immediately. The solution was poured into each well of a 24-well plate and solidified to prepare a sample for micro-MRI imaging. A T1-weighted image of the sample was taken by micro-MRI (4.7 T), manufactured by Oxford Instruments. The results taken by micro-MRI were shown in FIG. 7. In the case of the Gd-scFv cell/Gd+, the contrast of MR imaging was emphasized by an imaging effect (shortening of T1 relaxation-time of water molecules) of Gd-DTPA.

The following matters have been confirmed from the above results. The reporter vectors according to the embodiments were produced. Reporter peptides were extracellularly presented from reporter genes activated under specific conditions included in the produced reporter vectors. An MR image showing that cells labeled with the metallic compound specifically binding to the presented reporter peptides were enhanced by MRI measurement was obtained.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A method of detecting a cell having a specific condition, comprising:
    (1) incorporating a reporter vector into a target subject containing a cell,
    wherein the reporter vector comprises:
    a nucleotide sequence exhibiting a promoter activity depending on a specific condition;
    a nucleotide sequence encoding a single-chain antibody peptide presented extracellularly,
    wherein an amino acid sequence of the single-chain antibody peptide presented extracellularly comprises the amino acid sequence of SEQ ID NO: 1 or an amino acid sequence comprising the amino acid sequences of SEQ ID NOS: 3 and 5, or
    wherein the nucleotide sequence encoding a single-chain antibody peptide presented extracellularly comprises the nucleotide sequence of SEQ ID NO: 2 or a nucleotide sequence comprising the sequences of SEQ ID NOS: 4 and 6; and
    a nucleotide sequence encoding one or more transcription termination signals;
    in this order from upstream to downstream;
    (2) allowing the single-chain antibody peptide to be presented outside the cell;
    (3) bringing a metal capable of forming a binding pair with the single-chain antibody peptide into contact with the single-chain antibody peptide; and
    (4) detecting the metallic compound bound to the single-chain antibody peptide.

2. The method according to claim 1, wherein the target subject is at least one selected from the group consisting of an organ, internal organ, tissue, cell population, and a single cell collected from an individual animal.

3. The method according to claim 1, wherein the specific condition is cancer or abnormal bone metabolism.

4. The method according to claim 1,
    wherein the nucleotide sequence encoding a single-chain antibody peptide presented extracellularly comprises:
    (a) a nucleotide sequence encoding a single-chain antibody peptide,
    wherein an amino acid sequence of the single-chain antibody peptide comprises the amino acid sequence of SEQ ID NO: 1 or an amino acid sequence comprising the amino acid sequences of SEQ ID NOS: 3 and 5,
    wherein an amino acid sequence of the single-chain antibody peptide is the amino acid of SEQ ID NO: 1 or an amino acid comprising the amino acid sequences of SEQ ID NOS: 3 and 5, or
    wherein the nucleotide sequence encoding a single-chain antibody peptide comprises the sequence of SEQ ID NO: 2 or a nucleotide sequence comprising the sequences of SEQ ID NOS: 4 and 6;
    wherein the nucleotide sequence encoding a single-chain antibody peptide is a sequence of SEQ ID NO: 2 or a nucleotide sequence comprising the sequences of SEQ ID NOS: 4 and 6;
    (b) a nucleotide sequence encoding a signal peptide which transports the single-chain antibody peptide to a cell membrane; and (c) a nucleotide sequence encoding an anchor peptide which immobilizes the single-chain antibody peptide transported to the cell membrane by the signal peptide on the cell membrane;

in this order from upstream to downstream.

5. The method according to claim 4,
wherein the single-chain antibody peptide specifically binds to a specific metallic compound immunologically through its heavy chain variable region fragment and its light chain variable region fragment.

6. The method according to claim 4, wherein the single-chain antibody peptide in (a) specifically binds to a gadolinium compound.

7. The method according to claim 4,
wherein the single-chain antibody peptide in (a) specifically binds to a metallic compound selected from the group consisting of gadolinium, gadolinium ions, gadolinium complexes, gadolinium complex salts, metal oxides containing gadolinium, gadolinium oxide salts, gadolinium hydroxides, gadolinium carbonates, and hydrates of gadolinium.

8. The method according to claim 4,
wherein the single-chain antibody peptide in (a) specifically binds to gadopentetate.

9. The method according to claim 8,
wherein the nucleotide sequence encoding a single-chain antibody in (a) is a nucleotide sequence encoding a single-chain antibody peptide that specifically binds to gadopentetate.

10. The method according to claim 4,
wherein the nucleotide sequence encoding a signal peptide in (b) is a nucleotide encodes an Ig κ-chain leader peptide.

11. The method according to claim 4,
wherein the nucleotide sequence encoding an anchor peptide in (c) encodes an anchor peptide that immobilizes a platelet-derived growth factor receptor on a cell membrane.

12. The method according to claim 4,
wherein the nucleotide sequence encoding a single-chain antibody peptide presented extracellularly comprises:
(a) a nucleotide sequence encoding a single-chain antibody peptide specifically binding to gadopentetate,
wherein an amino acid sequence of the single-chain antibody peptide presented extracellularly comprises the amino acid sequence of SEQ ID NO: 1 or an amino acid sequence comprising the amino acid sequences of SEQ ID NOS: 3 and 5, or
wherein the nucleotide sequence encoding a single-chain antibody peptide presented extracellularly comprises the nucleotide sequence of SEQ ID NO: 2 or a nucleotide sequence comprising the sequences of SEQ ID NOS: 4 and 6;
(b) a nucleotide sequence encoding an Ig κ-chain leader peptide; and
(c) a nucleotide sequence encoding an anchor peptide that immobilizes a platelet-derived growth factor receptor on a cell membrane;
in this order from upstream to downstream.

13. The method according to claim 1, wherein the nucleotide sequence exhibiting a promoter activity depending on a specific condition is a nucleotide sequence configured to exhibit a promoter activity when a state or environment of the cell into which the reporter vector is introduced satisfies at least one predetermined specific condition.

14. The method according to claim 4, wherein the nucleotide sequence exhibiting a promoter activity depending on a specific condition is a nucleotide sequence configured to exhibit a promoter activity when a state or environment of the cell into which the reporter vector is introduced satisfies at least one predetermined a specific condition.

15. The method according to claim 12, wherein the nucleotide sequence exhibiting a promoter activity depending on a specific condition is a nucleotide sequence configured to exhibit a promoter activity when a state or environment of the cell into which the reporter vector is introduced satisfies at least one predetermined a specific condition.

16. A method of detecting a cell having a specific condition, comprising:
(1) incorporating a reporter vector into a target subject containing a cell,
wherein the reporter vector comprises:
a nucleotide sequence exhibiting a promoter activity depending on a specific condition;
a nucleotide sequence encoding a single-chain antibody peptide presented extracellularly,
wherein an amino acid sequence of the single-chain antibody peptide presented extracellularly comprises the amino acid sequence of SEQ ID NO: 9,
wherein an amino acid sequence of the single-chain antibody peptide presented extracellularly is the amino acid of SEQ ID NO: 9,
wherein the nucleotide sequence encoding a single-chain antibody peptide presented extracellularly comprises the nucleotide sequence of SEQ ID NO: 10, or
wherein the nucleotide sequence encoding a single-chain antibody peptide presented extracellularly is the nucleotide sequence of SEQ ID NO: 10; and
a nucleotide sequence encoding one or more transcription termination signals;
in this order from upstream to downstream;
(2) allowing the single-chain antibody peptide to be presented outside the cell;
(3) bringing a metal capable of forming a binding pair with the single-chain antibody peptide into contact with the single-chain antibody peptide; and
(4) detecting the metallic compound bound to the single-chain antibody peptide.

17. A method of detecting a cell having a specific condition, comprising:
(1) incorporating a reporter vector into a target subject containing a cell,
wherein the reporter vector comprises:
(A) a nucleotide sequence configured to exhibit a promoter activity when a state or environment of the cell into which the reporter vector is introduced satisfies at least one predetermined specific condition;
(B-a) a nucleotide sequence encoding a single-chain antibody peptide,
wherein an amino acid sequence of the single-chain antibody peptide presented extracellularly comprises the amino acid sequence of SEQ ID NO: 1 or an amino acid sequence comprising the amino acid sequences of SEQ ID NOS: 3 and 5, or
wherein the nucleotide sequence encoding a single-chain antibody peptide comprise the sequence of SEQ ID NO: 2 or a nucleotide sequence comprising the sequences of SEQ ID NOS: 4 and 6;
(B-b) a nucleotide sequence encoding an Ig κ-chain leader peptide which transports the single-chain antibody peptide to a cell membrane; and
(B-c) a nucleotide sequence encoding an anchor peptide that immobilizes a platelet-derived growth factor receptor on a cell membrane;

(C) a nucleotide sequence encoding one or more transcription termination signals;

in this order from upstream to downstream;

(2) allowing the single-chain antibody peptide to be presented outside the cell;

(3) bringing a metal capable of forming a binding pair with the single-chain antibody peptide into contact with the single-chain antibody peptide; and (4) detecting the metallic compound bound to the single-chain antibody peptide.

18. A method of detecting a cell having a specific condition, comprising:

(1) incorporating a reporter vector into a target subject containing a cell, wherein the reporter vector comprises:

(A) a nucleotide sequence configured to exhibit a promoter activity when a state or environment of the cell into which the reporter vector is introduced satisfies at least one predetermined specific condition;

(B) a nucleotide sequence encoding a single-chain antibody peptide presented extracellularly, wherein an amino acid sequence of the single-chain antibody peptide presented extracellularly comprises the amino acid sequence of SEQ ID NO: 9, wherein an amino acid sequence of the single-chain antibody peptide presented extracellularly is the amino acid sequence of SEQ ID NO: 9, wherein the nucleotide sequence encoding a single-chain antibody peptide presented extracellularly comprises the nucleotide sequence of SEQ ID NO: 10, or wherein the nucleotide sequence encoding a single-chain antibody peptide presented extracellularly is the nucleotide sequence of SEQ ID NO: 10, (C) a nucleotide sequence encoding one or more transcription termination signals;

in this order from upstream to downstream;

(2) allowing the single-chain antibody peptide to be presented outside the cell;

(3) bringing a metal capable of forming a binding pair with the single-chain antibody peptide into contact with the single-chain antibody peptide; and (4) detecting the metallic compound bound to the single-chain antibody peptide.

* * * * *

SEQUENCE LISTING

```
<160> NUMBER OF SEQ ID NOS: 10

<210> SEQ ID NO 1
<211> LENGTH: 231
<212> TYPE: PRT
<213> ORGANISM: Artificial Sequence
<220> FEATURE:
<223> OTHER INFORMATION: Description of Artificial Sequence:
      anti-Gd-DTPA scFv

<400> SEQUENCE: 1

Arg Ser Gln Leu Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Thr Trp Val Gln Glu Lys Pro Asp His Leu Phe Thr Gly
        35                  40                  45

Leu Ile Gly Gly Thr Lys Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Lys Leu Lys Ile Gly Gly Gly Gly
            100                 105                 110

Ser Gly Gly Gly Gly Ser Gly Gly Gly Gly Ser Leu Gln Gln Ser Gly
            115                 120                 125

Ala Glu Leu Val Lys Pro Gly Ala Ser Val Lys Leu Ser Cys Thr Ser
        130                 135                 140

Gly Leu Asn Ile Lys Asp Thr Tyr Ile Asn Trp Val Lys Gln Arg Pro
145                 150                 155                 160

Glu Gln Gly Leu Glu Trp Ile Gly Arg Ile Gly Pro Ala Asn Gly Asn
                165                 170                 175

Thr Lys Tyr Asp Pro Lys Phe Gln Gly Lys Ala Thr Leu Thr Ala Asp
            180                 185                 190

Thr Ser Ser Asn Thr Ala Tyr Leu Gln Leu Ser Ser Leu Thr Ser Glu
        195                 200                 205

Asp Thr Ala Val Tyr Tyr Cys Ser Arg Arg Trp Phe Phe Leu Tyr Trp
    210                 215                 220

Gly Gln Gly Thr Thr Val Thr
225                 230

<210> SEQ ID NO 2
<211> LENGTH: 693
<212> TYPE: DNA
<213> ORGANISM: Artificial Sequence
<220> FEATURE:
<223> OTHER INFORMATION: Description of Artificial Sequence:
      anti-Gd-DTPA scFv

<400> SEQUENCE: 2
agatctcagc tcactcaaga gtctgcctta acgaccagtc ctggggaaac cgtcaccctg     60
```

-continued

```
acatgtcggt ccagcaccgg agcggttacc actagcaact atgctacttg ggtgcaagag    120
aagcccgatc acctctttac agggcttatt ggcgggacta agaatcgagc acctggagta    180
ccggcaaggt ttagcggctc cctgataggt gacaaagccg ctttgaccat taccggggct    240
cagactgagg acgaagccat ctacttctgt gccctttggt actctaacca ttgggtgttt    300
ggaggcggga caaagctgaa gatcggcgga ggcgggtcag gcggcggtgg cagtggaggt    360
ggtgggagtc tccagcagtc tggagcagaa ctggtcaaac caggcgcgtc tgttaagctc    420
tcctgcacct caggtctgaa catcaaggac acgtacatca attgggtgaa acagcgtcca    480
gaacagggat tagagtggat tgggagaata ggtcccgcaa atggaaacac caaatatgac    540
cccaagttcc agggaaaagc cacgctaaca gccgatacat ccagcaatac cgcctatctg    600
cagttgtcca gcctgactag cgaggataca gctgtgtact actgctcaag acgctggttc    660
ttcctgtatt ggggccaagg cacaacagtg act                                 693
```

<210> SEQ ID NO 3
<211> LENGTH: 108
<212> TYPE: PRT
<213> ORGANISM: Artificial Sequence
<220> FEATURE:
<223> OTHER INFORMATION: Description of Artificial Sequence:
anti-Gd-DTPA VL

<400> SEQUENCE: 3

```
Arg Ser Gln Leu Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Thr Trp Val Gln Glu Lys Pro Asp His Leu Phe Thr Gly
        35                  40                  45

Leu Ile Gly Gly Thr Lys Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Lys Leu Lys Ile
            100                 105
```

<210> SEQ ID NO 4
<211> LENGTH: 324
<212> TYPE: DNA
<213> ORGANISM: Artificial Sequence
<220> FEATURE:
<223> OTHER INFORMATION: Description of Artificial Sequence:
anti-Gd-DTPA VL

<400> SEQUENCE: 4

```
agatctcagc tcactcaaga gtctgcctta acgaccagtc ctggggaaac cgtcaccctg     60
acatgtcggt ccagcaccgg agcggttacc actagcaact atgctacttg ggtgcaagag    120
aagcccgatc acctctttac agggcttatt ggcgggacta agaatcgagc acctggagta    180
ccggcaaggt ttagcggctc cctgataggt gacaaagccg ctttgaccat taccggggct    240
cagactgagg acgaagccat ctacttctgt gccctttggt actctaacca ttgggtgttt    300
ggaggcggga caaagctgaa gatc                                           324
```

<210> SEQ ID NO 5

```
<211> LENGTH: 108
<212> TYPE: PRT
<213> ORGANISM: Artificial Sequence
<220> FEATURE:
<223> OTHER INFORMATION: Description of Artificial Sequence:
      anti-Gd-DTPA VH

<400> SEQUENCE: 5

Leu Gln Gln Ser Gly Ala Glu Leu Val Lys Pro Gly Ala Ser Val Lys
1               5                   10                  15

Leu Ser Cys Thr Ser Gly Leu Asn Ile Lys Asp Thr Tyr Ile Asn Trp
            20                  25                  30

Val Lys Gln Arg Pro Glu Gln Gly Leu Glu Trp Ile Gly Arg Ile Gly
        35                  40                  45

Pro Ala Asn Gly Asn Thr Lys Tyr Asp Pro Lys Phe Gln Gly Lys Ala
    50                  55                  60

Thr Leu Thr Ala Asp Thr Ser Ser Asn Thr Ala Tyr Leu Gln Leu Ser
65                  70                  75                  80

Ser Leu Thr Ser Glu Asp Thr Ala Val Tyr Tyr Cys Ser Arg Arg Trp
                85                  90                  95

Phe Phe Leu Tyr Trp Gly Gln Gly Thr Thr Val Thr
            100                 105

<210> SEQ ID NO 6
<211> LENGTH: 324
<212> TYPE: DNA
<213> ORGANISM: Artificial Sequence
<220> FEATURE:
<223> OTHER INFORMATION: Description of Artificial Sequence:
      anti-Gd-DTPA VH

<400> SEQUENCE: 6
ctccagcagt ctggagcaga actggtcaaa ccaggcgcgt ctgttaagct ctcctgcacc      60
tcaggtctga acatcaagga cacgtacatc aattgggtga acagcgtcc agaacaggga     120 ttagagtgga ttgggagaat aggtcccgca aatggaaaca ccaaatatga ccccaagttc    180
cagggaaaag ccacgctaac agccgataca tccagcaata ccgcctatct gcagttgtcc    240
agcctgacta cgaggatac agctgtgtac tactgctcaa gacgctggtt cttcctgtat    300
tggggccaag gcacaacagt gact                                           324

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Linker
      peptide

<400> SEQUENCE: 7

Gly Gly Gly Gly Ser Gly Gly Gly Gly Ser Gly Gly Gly Gly Ser
1               5                   10                  15

<210> SEQ ID NO 8
<211> LENGTH: 45
<212> TYPE: DNA
<213> ORGANISM: Artificial Sequence
<220> FEATURE:
<223> OTHER INFORMATION: Description of Artificial Sequence: Linker
      peptide

<400> SEQUENCE: 8
ggcggaggcg gtcaggcgg cggtggcagt ggaggtggtg ggagt                      45
```

<210> SEQ ID NO 9
<211> LENGTH: 328
<212> TYPE: PRT
<213> ORGANISM: Artificial Sequence
<220> FEATURE:
<223> OTHER INFORMATION: Description of Artificial Sequence:
      anti-Gd-DTPA scFv

<400> SEQUENCE: 9

```
Met Glu Thr Asp Thr Leu Leu Leu Trp Val Leu Leu Leu Trp Val Pro
1               5                   10                  15

Gly Ser Thr Gly Asp Tyr Pro Tyr Asp Val Pro Asp Tyr Ala Gly Ala
            20                  25                  30

Gln Pro Ala Arg Ser Gln Leu Thr Gln Glu Ser Ala Leu Thr Thr Ser
        35                  40                  45

Pro Gly Glu Thr Val Thr Leu Thr Cys Arg Ser Ser Thr Gly Ala Val
    50                  55                  60

Thr Thr Ser Asn Tyr Ala Thr Trp Val Gln Glu Lys Pro Asp His Leu
65                  70                  75                  80

Phe Thr Gly Leu Ile Gly Gly Thr Lys Asn Arg Ala Pro Gly Val Pro
                85                  90                  95

Ala Arg Phe Ser Gly Ser Leu Ile Gly Asp Lys Ala Ala Leu Thr Ile
            100                 105                 110

Thr Gly Ala Gln Thr Glu Asp Glu Ala Ile Tyr Phe Cys Ala Leu Trp
        115                 120                 125

Tyr Ser Asn His Trp Val Phe Gly Gly Gly Thr Lys Leu Lys Ile Gly
130                 135                 140

Gly Gly Gly Ser Gly Gly Gly Ser Gly Gly Gly Ser Leu Gln
145                 150                 155                 160

Gln Ser Gly Ala Glu Leu Val Lys Pro Gly Ala Ser Val Lys Leu Ser
            165                 170                 175

Cys Thr Ser Gly Leu Asn Ile Lys Asp Thr Tyr Ile Asn Trp Val Lys
        180                 185                 190

Gln Arg Pro Glu Gln Gly Leu Glu Trp Ile Gly Arg Ile Gly Pro Ala
    195                 200                 205

Asn Gly Asn Thr Lys Tyr Asp Pro Lys Phe Gln Gly Lys Ala Thr Leu
210                 215                 220

Thr Ala Asp Thr Ser Ser Asn Thr Ala Tyr Leu Gln Leu Ser Ser Leu
225                 230                 235                 240

Thr Ser Glu Asp Thr Ala Val Tyr Tyr Cys Ser Arg Arg Trp Phe Phe
                245                 250                 255

Leu Tyr Trp Gly Gln Gly Thr Thr Val Thr Val Asp Glu Gln Lys Leu
            260                 265                 270

Ile Ser Glu Glu Asp Leu Asn Ala Val Gly Gln Asp Thr Gln Glu Val
        275                 280                 285

Ile Val Val Pro His Ser Leu Pro Phe Lys Val Val Ile Ser Ala
    290                 295                 300

Ile Leu Ala Leu Val Val Leu Thr Ile Ile Ser Leu Ile Ile Leu Ile
305                 310                 315                 320

Met Leu Trp Gln Lys Lys Pro Arg
                325
```

<210> SEQ ID NO 10
<211> LENGTH: 987
<212> TYPE: DNA

<213> ORGANISM: Artificial Sequence
<220> FEATURE:
<223> OTHER INFORMATION: Description of Artificial Sequence:
    anti-Gd-DTPA scFv

<400> SEQUENCE: 10

```
atggagacag acacactcct gctatgggta ctgctgctct gggttccagg ttccactggt      60
gactatccat atgatgttcc agattatgct ggggcccagc cggccagatc tcagctcact     120
caagagtctg ccttaacgac cagtcctggg gaaaccgtca ccctgacatg tcggtccagc     180
accggagcgg ttaccactag caactatgct acttgggtgc aagagaagcc cgatcacctc     240 tttcagggc ttattggcgg gactaagaat cgagcacctg gagtaccggc aaggtttagc      300
ggctccctga taggtgacaa agccgctttg accattaccg gggctcagac tgaggacgaa     360
gccatctact tctgtgccct ttggtactct aaccattggg tgtttggagg cgggacaaag     420
ctgaagatcg gcggaggcgg gtcaggcggc ggtggcagtg gaggtggtgg gagtctccag     480
cagtctggag cagaactggt caaaccaggc gcgtctgtta agctctcctg cacctcaggt     540
ctgaacatca aggacacgta catcaattgg gtgaaacagc gtccagaaca gggattagag     600
tggattggga aataggtcc cgcaaatgga acaccaaat atgaccccaa gttccaggga      660
aaagccacgc taacagccga tacatccagc aataccgcct atctgcagtt gtccagcctg     720
actagcgagg atacagctgt gtactactgc tcaagacgct ggttcttcct gtattggggc     780
caaggcacaa cagtgactgt cgacgaacaa aaactcatct cagaagagga tctgaatgct     840
gtgggccagg acacgcagga ggtcatcgtg gtgccacact ccttgcccct taaggtggtg     900
gtgatctcag ccatcctggc cctggtggtg ctcaccatca tctcccttat catcctcatc     960
atgctttggc agaagaagcc acgttag                                         987
```